US010456211B2

(12) United States Patent
McAfee

(10) Patent No.: US 10,456,211 B2
(45) Date of Patent: Oct. 29, 2019

(54) METHODS AND APPARATUS FOR SPINAL RECONSTRUCTIVE SURGERY AND MEASURING SPINAL LENGTH AND INTERVERTEBRAL SPACING, TENSION AND ROTATION

(71) Applicant: Medicrea International, Rillieux la Pape (FR)

(72) Inventor: Paul C. McAfee, Sparks, MD (US)

(73) Assignee: Medicrea International, Rillieux la Pape (FR)

( * ) Notice: Subject to any disclaimer, the term of this patent is extended or adjusted under 35 U.S.C. 154(b) by 165 days.

(21) Appl. No.: 15/344,320

(22) Filed: Nov. 4, 2016

(65) Prior Publication Data

US 2018/0125598 A1  May 10, 2018
US 2018/0228566 A9  Aug. 16, 2018

Related U.S. Application Data

(60) Provisional application No. 62/250,743, filed on Nov. 4, 2015, provisional application No. 62/413,159, filed on Oct. 26, 2016.

(51) Int. Cl.
*A61B 90/00* (2016.01)
*A61B 17/02* (2006.01)

(52) U.S. Cl.
CPC ............ *A61B 90/06* (2016.02); *A61B 17/025* (2013.01); *A61B 2017/0256* (2013.01); *A61B 2090/061* (2016.02); *A61B 2090/067* (2016.02)

(58) Field of Classification Search
CPC ........ A61B 17/02; A61B 17/86; A61B 17/025; A61B 90/06
See application file for complete search history.

(56) References Cited

U.S. PATENT DOCUMENTS

| 5,006,984 A | 4/1991 | Steele |
| 5,163,440 A | 11/1992 | DeLuca et al. |
| 5,224,035 A | 6/1993 | Yamashita et al. |
| 5,251,127 A | 10/1993 | Raab |

(Continued)

FOREIGN PATENT DOCUMENTS

| AU | 2015258176 | 12/2015 |
| AU | 2015202416 | 3/2017 |

(Continued)

OTHER PUBLICATIONS

US 9,451,972 B2, 09/2016, Lang et al. (withdrawn)

(Continued)

*Primary Examiner* — Christopher J Beccia
(74) *Attorney, Agent, or Firm* — Knobbe, Martens, Olson & Bear, LLP

(57) ABSTRACT

Methods and apparatus are disclosed for performing spinal reconstructive surgery, including measuring spinal length in the Y-axis at the middle column, measuring intervertebral spacing in the Y-axis at the middle column, measuring intervertebral tension applied to the posterior longitudinal ligament, establishing the height of intervertebral spacers along the Y-axis at the middle column based on one or more of such measurements, measuring intervertebral rotation around the Y-axis, and measuring flexion-extension or anterior-posterior rotation around the X-axis.

15 Claims, 37 Drawing Sheets

(56) References Cited

U.S. PATENT DOCUMENTS

| | | |
|---|---|---|
| 5,291,901 A | 3/1994 | Graf |
| 5,305,203 A | 4/1994 | Raab |
| 5,312,405 A | 5/1994 | Korotko et al. |
| 5,413,116 A | 5/1995 | Radke et al. |
| 5,514,180 A | 5/1996 | Heggeness |
| 5,667,506 A | 9/1997 | Sutterlin |
| 5,748,767 A | 5/1998 | Raab |
| 5,785,663 A | 7/1998 | Sarvazyan |
| 6,015,409 A | 1/2000 | Jackson |
| 6,213,958 B1 | 4/2001 | Winder |
| 6,282,437 B1 | 8/2001 | Franck et al. |
| 6,364,849 B1 | 4/2002 | Wilcox |
| 6,385,475 B1 | 5/2002 | Cinquin et al. |
| 6,409,684 B1 | 6/2002 | Wilk |
| 6,443,953 B1 | 9/2002 | Perra et al. |
| 6,499,488 B1 | 12/2002 | Hunter et al. |
| 6,565,519 B2 | 5/2003 | Benesh |
| 6,585,666 B2 | 7/2003 | Suh et al. |
| 6,711,432 B1 | 3/2004 | Krause et al. |
| 6,715,213 B2 | 4/2004 | Richter |
| 6,716,213 B2 | 4/2004 | Shitoto |
| 6,746,449 B2 | 6/2004 | Jones et al. |
| 6,786,930 B2 | 9/2004 | Biscup |
| 7,066,938 B2 | 6/2006 | Slivka et al. |
| 7,338,526 B2 | 3/2008 | Steinberg et al. |
| 7,509,183 B2 | 3/2009 | Lin |
| 7,534,263 B2 | 5/2009 | Burdulis |
| 7,606,613 B2 | 10/2009 | Simon et al. |
| 7,611,522 B2 | 11/2009 | Gorek |
| 7,618,451 B2 | 11/2009 | Fitz et al. |
| 7,634,119 B2 | 12/2009 | Tsougarakis et al. |
| 7,635,367 B2 | 12/2009 | Groiso |
| 7,660,623 B2 | 2/2010 | Hunter et al. |
| 7,674,293 B2 | 3/2010 | Kuiper et al. |
| 7,715,602 B2 | 5/2010 | Richard |
| 7,763,054 B2 | 7/2010 | Clement et al. |
| 7,824,413 B2 | 11/2010 | Varieur et al. |
| 7,835,778 B2 | 11/2010 | Foley et al. |
| 7,840,253 B2 | 11/2010 | Tremblay et al. |
| 7,862,593 B2 | 1/2011 | Clement et al. |
| 7,918,887 B2 | 4/2011 | Roche |
| 7,953,471 B2 | 5/2011 | Clayton et al. |
| 7,981,158 B2 | 7/2011 | Fitz et al. |
| 7,996,061 B2 | 8/2011 | Mollard et al. |
| 7,996,064 B2 | 8/2011 | Simon et al. |
| 8,000,926 B2 | 8/2011 | Roche et al. |
| 8,046,050 B2 | 10/2011 | Govari et al. |
| 8,066,708 B2 | 11/2011 | Lang et al. |
| 8,077,950 B2 | 12/2011 | Tsougarakis et al. |
| 8,083,778 B2 | 12/2011 | Clement et al. |
| 8,105,330 B2 | 1/2012 | Fitz et al. |
| 8,142,842 B2 | 3/2012 | Nicholas et al. |
| 8,196,825 B2 | 6/2012 | Turner et al. |
| 8,211,109 B2 | 7/2012 | Groiso |
| 8,241,296 B2 | 8/2012 | Wasielewski |
| 8,246,680 B2 | 8/2012 | Betz et al. |
| 8,265,790 B2 | 9/2012 | Amiot et al. |
| 8,270,253 B1 | 9/2012 | Roche et al. |
| 8,275,594 B2 | 9/2012 | Lin et al. |
| 8,308,772 B2 | 11/2012 | Clement et al. |
| 8,308,775 B2 | 11/2012 | Clement et al. |
| 8,337,501 B2 | 12/2012 | Fitz et al. |
| 8,372,075 B2 | 2/2013 | Groiso |
| 8,377,073 B2 | 2/2013 | Wasielewski |
| 8,394,142 B2 | 3/2013 | Berg et al. |
| 8,398,681 B2 | 3/2013 | Augostino et al. |
| 8,400,312 B2 | 3/2013 | Hotokebuchi et al. |
| 8,414,592 B2 | 4/2013 | Quirno |
| 8,442,621 B2 | 5/2013 | Gorek et al. |
| 8,465,527 B2 | 6/2013 | Clement |
| 8,494,805 B2 | 7/2013 | Roche et al. |
| 8,506,632 B2 | 8/2013 | Ganem et al. |
| 8,532,806 B1 | 9/2013 | Masson |
| 8,535,337 B2 | 9/2013 | Chang et al. |
| 8,556,983 B2 | 10/2013 | Bojarski et al. |
| 8,562,617 B2 | 10/2013 | Chessar et al. |
| 8,588,892 B2 | 11/2013 | Hladio et al. |
| 8,636,776 B2 | 1/2014 | Rosenberg et al. |
| 8,672,948 B2 | 3/2014 | Lemaitre |
| 8,685,093 B2 | 4/2014 | Anderson et al. |
| 8,690,888 B2 | 4/2014 | Stein et al. |
| 8,718,820 B2 | 5/2014 | Amiot et al. |
| 8,758,357 B2 | 6/2014 | Frey |
| 8,777,877 B2 | 7/2014 | Stein et al. |
| 8,784,339 B2 | 7/2014 | Stein et al. |
| 8,801,786 B2 | 8/2014 | Bernard et al. |
| 8,814,877 B2 | 8/2014 | Wasielewski |
| 8,852,237 B2 | 10/2014 | Kalfas et al. |
| 8,855,389 B1 | 10/2014 | Hoffman et al. |
| 8,864,764 B2 | 10/2014 | Groiso |
| 8,870,889 B2 | 10/2014 | Frey |
| 8,900,316 B2 | 12/2014 | Lenz |
| 8,911,448 B2 | 12/2014 | Stein |
| 8,926,673 B2 | 1/2015 | Clement et al. |
| 8,945,133 B2 | 2/2015 | Stein et al. |
| 8,956,416 B2 | 2/2015 | McCarthy |
| 8,974,467 B2 | 3/2015 | Stone |
| 8,983,813 B2 | 3/2015 | Miles et al. |
| 8,998,962 B2 | 4/2015 | Birch |
| 9,011,448 B2 | 4/2015 | Roche et al. |
| 9,034,037 B2 | 5/2015 | Fiere et al. |
| 9,039,772 B2 | 5/2015 | Park et al. |
| 9,056,017 B2 | 6/2015 | Kotlus |
| 9,066,701 B1 | 6/2015 | Finley et al. |
| 9,066,734 B2 | 6/2015 | Schoenfeld et al. |
| 9,078,755 B2 | 7/2015 | Mahfouz |
| 9,101,492 B2 | 8/2015 | Mangione et al. |
| 9,115,998 B2 | 8/2015 | Proulx et al. |
| 9,119,572 B2 | 9/2015 | Gorek et al. |
| 9,119,671 B2 | 9/2015 | Kast |
| 9,125,680 B2 | 9/2015 | Kostrzewski et al. |
| 9,144,440 B2 | 9/2015 | Aminian |
| 9,144,470 B2 | 9/2015 | Proulx et al. |
| 9,168,153 B2 | 10/2015 | Bettenga |
| 9,173,661 B2 | 11/2015 | Metzger et al. |
| 9,180,015 B2 | 11/2015 | Fitz et al. |
| 9,192,412 B2 | 11/2015 | Meyrat et al. |
| 9,198,678 B2 | 12/2015 | Frey et al. |
| 9,232,955 B2 | 1/2016 | Bonin, Jr. et al. |
| 9,233,001 B2 | 1/2016 | Miles et al. |
| 9,237,952 B2 | 1/2016 | Kurtz |
| 9,248,023 B2 | 2/2016 | Ries et al. |
| 9,250,620 B2 | 2/2016 | Kotlus |
| 9,278,010 B2 | 3/2016 | Gibson et al. |
| 9,283,048 B2 | 3/2016 | Kostrzewski et al. |
| 9,289,221 B2 | 3/2016 | Gelaude et al. |
| 9,289,270 B2 | 3/2016 | Gielen et al. |
| 9,295,482 B2 | 3/2016 | Fitz et al. |
| 9,295,497 B2 | 3/2016 | Schoenfeld et al. |
| 9,295,561 B2 | 3/2016 | Ball et al. |
| 9,301,768 B2 | 4/2016 | Buza et al. |
| 9,308,050 B2 | 4/2016 | Kostrzewski et al. |
| 9,308,091 B2 | 4/2016 | Lang |
| 9,314,275 B2 | 4/2016 | Clement et al. |
| 9,314,343 B2 | 4/2016 | Parisi et al. |
| 9,320,547 B2 | 4/2016 | Augostino |
| 9,320,604 B2 | 4/2016 | Miles et al. |
| 9,326,780 B2 | 5/2016 | Wong et al. |
| 9,339,277 B2 | 5/2016 | Jansen et al. |
| 9,345,492 B2 | 5/2016 | Stein et al. |
| 9,358,051 B2 | 6/2016 | Sournac et al. |
| 9,358,130 B2 | 6/2016 | Livorsi et al. |
| 9,358,136 B2 | 6/2016 | Stein et al. |
| 9,364,370 B2 | 6/2016 | Kühnel |
| 9,381,085 B2 | 7/2016 | Axelson et al. |
| 9,387,015 B2 | 7/2016 | Taylor |
| 9,392,953 B1 | 7/2016 | Gharib |
| 9,393,052 B2 | 7/2016 | Berg et al. |
| 9,402,726 B2 | 8/2016 | Linderman et al. |
| 9,408,615 B2 | 8/2016 | Fitz et al. |
| 9,408,642 B2 | 8/2016 | Wong et al. |
| 9,408,698 B2 | 8/2016 | Miles et al. |
| 9,414,940 B2 | 8/2016 | Stein et al. |
| 9,433,443 B2 | 9/2016 | Montello et al. |

(56) References Cited

U.S. PATENT DOCUMENTS

| | | |
|---|---|---|
| 9,439,659 B2 | 9/2016 | Schoenefeld et al. |
| 9,439,767 B2 | 9/2016 | Bojarski et al. |
| 9,439,781 B2 | 9/2016 | Gibson |
| 9,445,913 B2 | 9/2016 | Donner et al. |
| 9,452,022 B2 | 9/2016 | McIntosh et al. |
| 9,452,023 B2 | 9/2016 | Boillot et al. |
| 9,452,050 B2 | 9/2016 | Miles et al. |
| 9,452,064 B2 | 9/2016 | Trautwein et al. |
| 9,468,436 B2 | 10/2016 | Groiso |
| 9,468,502 B2 | 10/2016 | Wiebe et al. |
| 9,491,415 B2 | 11/2016 | Deitz et al. |
| 9,492,183 B2 | 11/2016 | Wilkinson et al. |
| 9,495,483 B2 | 11/2016 | Steines et al. |
| 9,495,509 B2 | 11/2016 | Amiot et al. |
| 9,498,260 B2 | 11/2016 | Funk et al. |
| 9,504,502 B2 | 11/2016 | Kuiper et al. |
| 9,510,864 B2 | 12/2016 | Devito |
| 9,517,134 B2 | 12/2016 | Lang |
| 9,517,143 B2 | 12/2016 | Prevost et al. |
| 9,526,514 B2 | 12/2016 | Kelley et al. |
| 9,532,730 B2 | 1/2017 | Wasielewski |
| 9,539,031 B2 | 1/2017 | Fauth |
| 9,539,116 B2 | 1/2017 | Claypool et al. |
| 9,539,760 B2 | 1/2017 | Stahl et al. |
| 9,549,782 B2 | 1/2017 | Park et al. |
| 9,554,411 B1 | 1/2017 | Hall et al. |
| 9,554,910 B2 | 1/2017 | Vanasse et al. |
| 9,561,115 B2 | 2/2017 | Elahinia et al. |
| 9,566,075 B2 | 2/2017 | Carroll |
| 9,579,043 B2 | 2/2017 | Chien et al. |
| 9,585,597 B2 | 3/2017 | McCaullet et al. |
| 9,597,096 B2 | 3/2017 | Aghazadeh |
| 9,597,156 B2 | 3/2017 | Amiot et al. |
| 9,603,613 B2 | 3/2017 | Schoenefeld et al. |
| 9,603,623 B2 | 3/2017 | Brooks et al. |
| 9,603,711 B2 | 3/2017 | Bojarski et al. |
| 9,610,086 B2 | 4/2017 | Park et al. |
| 9,615,834 B2 | 4/2017 | Agmihotri et al. |
| 9,622,712 B2 | 4/2017 | Munro et al. |
| 9,629,723 B2 | 4/2017 | Parisi et al. |
| 9,642,633 B2 | 5/2017 | Frey et al. |
| 9,655,729 B2 | 5/2017 | Parisi et al. |
| 9,662,214 B2 | 5/2017 | Li et al. |
| 9,668,748 B2 | 6/2017 | McKinnon et al. |
| 9,668,873 B2 | 6/2017 | Winslow |
| 9,675,471 B2 | 6/2017 | Bojarski et al. |
| 9,693,831 B2 | 7/2017 | Mosnier |
| 9,757,072 B1 | 9/2017 | Urbalejo |
| 9,782,228 B2 | 10/2017 | Mosnier et al. |
| 9,649,170 B2 | 12/2017 | Park et al. |
| 9,968,408 B1 | 5/2018 | Casey et al. |
| 9,987,048 B2 | 6/2018 | Mosnier et al. |
| 9,993,177 B2 | 6/2018 | Chien et al. |
| 10,045,824 B2 | 8/2018 | Mosnier et al. |
| 10,314,657 B2 | 6/2019 | Mosnier et al. |
| 2002/0035321 A1 | 3/2002 | Bucholz et al. |
| 2002/0038118 A1 | 3/2002 | Shoham |
| 2002/0045812 A1 | 4/2002 | Ben-Haim et al. |
| 2002/0103432 A1 | 8/2002 | Kawchuk |
| 2003/0191383 A1 | 10/2003 | Ben-Haim et al. |
| 2004/0120781 A1 | 6/2004 | Luca |
| 2004/0143243 A1 | 7/2004 | Wahrburg |
| 2004/0152972 A1 | 8/2004 | Hunter |
| 2004/0167637 A1 | 8/2004 | Biscup |
| 2004/0215190 A1 | 10/2004 | Nguyen et al. |
| 2004/0243148 A1 | 12/2004 | Wasuekewski |
| 2004/0267279 A1* | 12/2004 | Casutt ............... A61B 90/06 606/104 |
| 2005/0149050 A1 | 7/2005 | Stifter et al. |
| 2005/0177239 A1 | 8/2005 | Steinberg |
| 2005/0182320 A1 | 8/2005 | Stifter et al. |
| 2005/0182454 A1 | 8/2005 | Kaula et al. |
| 2005/0203531 A1 | 9/2005 | Lakin et al. |
| 2005/0203532 A1 | 9/2005 | Ferguson et al. |
| 2005/0262911 A1 | 12/2005 | Dankowicz et al. |
| 2006/0015018 A1 | 1/2006 | Jutras et al. |
| 2006/0015030 A1 | 1/2006 | Poulin et al. |
| 2006/0069324 A1 | 3/2006 | Block et al. |
| 2006/0074431 A1 | 4/2006 | Sutton et al. |
| 2006/0136058 A1 | 6/2006 | Pietrzak |
| 2006/0285991 A1 | 12/2006 | McKinley |
| 2006/0287627 A1 | 12/2006 | Johnson |
| 2007/0021682 A1 | 1/2007 | Gharib et al. |
| 2007/0118243 A1 | 5/2007 | Schroeder et al. |
| 2007/0225731 A1 | 9/2007 | Couture et al. |
| 2008/0058945 A1 | 3/2008 | Hajaj et al. |
| 2008/0079546 A1 | 4/2008 | Sensomatic |
| 2008/0108991 A1 | 5/2008 | von Jako |
| 2008/0255575 A1* | 10/2008 | Justis ............... A61B 90/06 606/102 |
| 2009/0024164 A1 | 1/2009 | Neubardt |
| 2009/0194206 A1 | 8/2009 | Jeon et al. |
| 2009/0204159 A1 | 8/2009 | Justis et al. |
| 2009/0254326 A1 | 10/2009 | Isaacs |
| 2010/0042157 A1 | 2/2010 | Trieu |
| 2010/0100011 A1 | 4/2010 | Roche |
| 2010/0183201 A1 | 7/2010 | Schwab et al. |
| 2010/0191071 A1 | 7/2010 | Anderson et al. |
| 2010/0217270 A1 | 8/2010 | Polinski et al. |
| 2010/0217336 A1 | 8/2010 | Crawford et al. |
| 2011/0004309 A9 | 3/2011 | Bojarski et al. |
| 2011/0071802 A1 | 3/2011 | Bojarski et al. |
| 2011/0118740 A1 | 5/2011 | Rabiner et al. |
| 2011/0172566 A1 | 7/2011 | Kawchuk |
| 2011/0214279 A1 | 9/2011 | Park et al. |
| 2011/0224796 A1 | 9/2011 | Weiland et al. |
| 2011/0257653 A1 | 10/2011 | Hughes et al. |
| 2011/0257657 A1 | 10/2011 | Turner et al. |
| 2011/0295159 A1 | 12/2011 | Shachar et al. |
| 2011/0306873 A1 | 12/2011 | Shenai et al. |
| 2012/0022357 A1 | 1/2012 | Chang et al. |
| 2012/0035611 A1 | 2/2012 | Kave |
| 2012/0123301 A1 | 5/2012 | Connor et al. |
| 2012/0143090 A1 | 6/2012 | Hay et al. |
| 2012/0172884 A1 | 7/2012 | Zheng et al. |
| 2012/0203289 A1 | 8/2012 | Beerens et al. |
| 2012/0323327 A1 | 12/2012 | McAfee |
| 2013/0079678 A1 | 3/2013 | Stein et al. |
| 2013/0079679 A1 | 3/2013 | Roche et al. |
| 2013/0079790 A1 | 3/2013 | Stein et al. |
| 2013/0131486 A1 | 5/2013 | Copf et al. |
| 2013/0345718 A1 | 6/2013 | Crawford et al. |
| 2013/0211531 A1 | 8/2013 | Steines et al. |
| 2013/0245631 A1 | 9/2013 | Bettenga |
| 2013/0253599 A1 | 9/2013 | Gorek et al. |
| 2013/0303883 A1 | 11/2013 | Zehavi et al. |
| 2014/0100579 A1 | 4/2014 | Kelman et al. |
| 2014/0135658 A1 | 5/2014 | Hladio et al. |
| 2014/0180415 A1 | 6/2014 | Koss |
| 2014/0194889 A1 | 7/2014 | Chang et al. |
| 2014/0228670 A1 | 8/2014 | Justis et al. |
| 2014/0228860 A1 | 8/2014 | Steines et al. |
| 2014/0244220 A1 | 8/2014 | McKinnon et al. |
| 2014/0257402 A1 | 9/2014 | Barsoum |
| 2014/0272881 A1 | 9/2014 | Barsoum |
| 2014/0296860 A1 | 10/2014 | Stein et al. |
| 2014/0303672 A1 | 10/2014 | Tran et al. |
| 2014/0316468 A1 | 10/2014 | Keiser et al. |
| 2015/0057756 A1 | 2/2015 | Lang et al. |
| 2015/0066145 A1 | 3/2015 | Rogers et al. |
| 2015/0080901 A1 | 3/2015 | Stein |
| 2015/0081029 A1 | 3/2015 | Bojarski et al. |
| 2015/0088030 A1 | 3/2015 | Gharib et al. |
| 2015/0100066 A1 | 4/2015 | Kostrezewski et al. |
| 2015/0100091 A1 | 4/2015 | Tohmeh et al. |
| 2015/0105782 A1 | 4/2015 | D'Lima et al. |
| 2015/0127055 A1 | 5/2015 | Dvorak et al. |
| 2015/0150646 A1 | 6/2015 | Pryor et al. |
| 2015/0164657 A1 | 6/2015 | Miles et al. |
| 2015/0182292 A1 | 7/2015 | Hladio et al. |
| 2015/0223900 A1 | 8/2015 | Wiebe et al. |
| 2015/0245844 A1 | 9/2015 | Kennedy et al. |
| 2015/0250597 A1 | 9/2015 | Lang et al. |
| 2015/0265291 A1 | 9/2015 | Wilkinson |

(56) References Cited

U.S. PATENT DOCUMENTS

| | | |
|---|---|---|
| 2015/0305878 A1 | 10/2015 | O'Neil et al. |
| 2015/0305891 A1 | 10/2015 | Bergin et al. |
| 2015/0313723 A1 | 11/2015 | Jansen et al. |
| 2015/0328004 A1 | 11/2015 | Mafhouz |
| 2015/0366630 A1 | 12/2015 | Gorek et al. |
| 2016/0000571 A1 | 1/2016 | Mahfouz |
| 2016/0007983 A1 | 1/2016 | Frey et al. |
| 2016/0015465 A1 | 1/2016 | Steines et al. |
| 2016/0022176 A1 | 1/2016 | Le Huec et al. |
| 2016/0022370 A1 | 1/2016 | Pavlovskaia et al. |
| 2016/0038161 A1 | 2/2016 | Gibson |
| 2016/0038238 A1 | 2/2016 | Kostrzewski et al. |
| 2016/0038242 A1 | 2/2016 | Lo Iacono et al. |
| 2016/0038293 A1 | 2/2016 | Slamin |
| 2016/0038307 A1 | 2/2016 | Bettenga |
| 2016/0045230 A1 | 2/2016 | Lowery et al. |
| 2016/0045317 A1 | 2/2016 | Lang et al. |
| 2016/0045326 A1 | 2/2016 | Hansen et al. |
| 2016/0058320 A1 | 3/2016 | Chien et al. |
| 2016/0058523 A1 | 3/2016 | Chien et al. |
| 2016/0074052 A1 | 3/2016 | Keppler et al. |
| 2016/0074202 A1 | 3/2016 | Reed et al. |
| 2016/0081754 A1 | 3/2016 | Kostrzewski et al. |
| 2016/0095710 A1 | 4/2016 | Juszczyk et al. |
| 2016/0100907 A1 | 4/2016 | Gomes |
| 2016/0106483 A1 | 4/2016 | Mayer et al. |
| 2016/0128847 A1 | 5/2016 | Kurtaliaj et al. |
| 2016/0143744 A1 | 5/2016 | Bojarski et al. |
| 2016/0157751 A1 | 6/2016 | Mahfouz |
| 2016/0199101 A1 | 7/2016 | Sharifi-Mehr et al. |
| 2016/0210374 A1 | 7/2016 | Mosnier |
| 2016/0228192 A1 | 8/2016 | Jansen et al. |
| 2016/0235480 A1 | 8/2016 | Scholl et al. |
| 2016/0235493 A1 | 8/2016 | LeBoeuf, II et al. |
| 2016/0242857 A1 | 8/2016 | Scholl |
| 2016/0242934 A1 | 8/2016 | Van der Walt et al. |
| 2016/0256279 A1 | 9/2016 | Sanders et al. |
| 2016/0256285 A1 | 9/2016 | Jansen |
| 2016/0262800 A1 | 9/2016 | Scholl et al. |
| 2016/0262895 A1 | 9/2016 | Shea et al. |
| 2016/0270802 A1 | 9/2016 | Fang et al. |
| 2016/0270931 A1 | 9/2016 | Trieu |
| 2016/0274571 A1 | 9/2016 | LaVallee et al. |
| 2016/0283676 A1 | 9/2016 | Kelly et al. |
| 2016/0287395 A1 | 10/2016 | Khalili et al. |
| 2016/0296285 A1 | 10/2016 | Chaoui et al. |
| 2016/0310221 A1 | 10/2016 | Bar et al. |
| 2016/0331417 A1 | 11/2016 | Trautwein et al. |
| 2016/0354009 A1 | 12/2016 | Schroeder |
| 2016/0354161 A1 | 12/2016 | Deitz |
| 2016/0360997 A1 | 12/2016 | Yadav et al. |
| 2017/0000568 A1 | 1/2017 | O'Neil et al. |
| 2017/0007145 A1 | 1/2017 | Gharib et al. |
| 2017/0007328 A1 | 1/2017 | Cattin et al. |
| 2017/0007408 A1 | 1/2017 | Fitz et al. |
| 2017/0027590 A1 | 2/2017 | Amiot et al. |
| 2017/0027617 A1 | 2/2017 | Strnad |
| 2017/0035580 A1 | 2/2017 | Murphy |
| 2017/0056179 A1 | 3/2017 | Lorio |
| 2017/0056196 A1 | 3/2017 | Kuiper et al. |
| 2017/0071503 A1 | 3/2017 | Wasiewlewski |
| 2017/0119472 A1 | 5/2017 | Herrmann et al. |
| 2017/0132389 A1 | 5/2017 | McCaulley et al. |
| 2017/0135706 A1 | 5/2017 | Frey et al. |
| 2017/0135707 A9 | 5/2017 | Frey et al. |
| 2017/0143426 A1 | 5/2017 | Isaacs et al. |
| 2017/0143494 A1 | 5/2017 | Mahfouz |
| 2017/0143502 A1 | 5/2017 | Yadin et al. |
| 2017/0156798 A1 | 6/2017 | Wasielewski |
| 2017/0189121 A1 | 7/2017 | Frasier et al. |
| 2017/0245937 A1 | 8/2017 | Mosnier |
| 2017/0252107 A1 | 9/2017 | Turner et al. |
| 2018/0132942 A1 | 5/2018 | Mosnier et al. |
| 2018/0178148 A1 | 6/2018 | Mazor et al. |
| 2018/0256067 A1 | 9/2018 | Chen et al. |
| 2018/0289396 A1 | 10/2018 | McGahan et al. |
| 2018/0295584 A1 | 10/2018 | Gliner et al. |
| 2018/0303552 A1 | 10/2018 | Ryan et al. |
| 2019/0069956 A1 | 3/2019 | Ryan et al. |

FOREIGN PATENT DOCUMENTS

| | | |
|---|---|---|
| CN | 1816134 | 8/2006 |
| CN | 102805677 | 12/2012 |
| CN | 104127229 | 11/2014 |
| CN | 205073000 | 3/2016 |
| CN | 103892953 | 5/2016 |
| CN | 104323843 | 1/2017 |
| CN | 104434287 | 1/2017 |
| CN | 105078555 | 11/2018 |
| EP | 1570781 | 9/2005 |
| EP | 2 053 580 | 4/2009 |
| EP | 2749235 | 7/2014 |
| EP | 2754419 | 7/2014 |
| EP | 2496183 | 9/2015 |
| EP | 3000443 | 3/2016 |
| EP | 2608749 | 8/2016 |
| EP | 2403434 | 4/2017 |
| EP | 3 431 032 | 1/2019 |
| FR | 1358988 | 4/1964 |
| FR | 1360208 | 5/1964 |
| JP | 2016-537036 | 12/2016 |
| JP | 2016-540610 | 12/2016 |
| SU | 1497721 | 7/1979 |
| SU | 1704102 | 1/1992 |
| WO | WO98/55038 | 12/1998 |
| WO | WO 00/53077 | 9/2000 |
| WO | WO2004/017836 | 3/2004 |
| WO | 2004089224 | 10/2004 |
| WO | WO2004/089224 | 10/2004 |
| WO | WO 05/074368 | 8/2005 |
| WO | WO 06/075331 | 7/2006 |
| WO | WO 06/084193 | 8/2006 |
| WO | WO 07/035925 | 3/2007 |
| WO | WO 07/038290 | 4/2007 |
| WO | WO 08/002588 | 1/2008 |
| WO | WO2008/079546 | 7/2008 |
| WO | WO 08/124079 | 10/2008 |
| WO | WO2009119181 | 10/2009 |
| WO | WO 10/044880 | 4/2010 |
| WO | WO 10/064234 | 6/2010 |
| WO | WO2010/121147 | 10/2010 |
| WO | WO 10/147972 | 12/2010 |
| WO | WO 11/021192 | 2/2011 |
| WO | WO2012/012863 | 2/2012 |
| WO | WO 12/131660 | 10/2012 |
| WO | WO2013/003435 | 1/2013 |
| WO | WO2016102026 | 12/2014 |
| WO | WO2015/040552 | 3/2015 |
| WO | WO2015/056131 | 4/2015 |
| WO | WO2015/079011 | 6/2015 |
| WO | WO2015/089118 | 6/2015 |
| WO | WO2015185219 | 6/2015 |
| WO | WO2016044352 | 9/2015 |
| WO | WO 15/195843 | 12/2015 |
| WO | WO2015/200720 | 12/2015 |
| WO | WO2016088130 | 12/2015 |
| WO | WO 2016/012726 | 1/2016 |
| WO | WO2016/019424 | 2/2016 |
| WO | WO2016/019425 | 2/2016 |
| WO | WO2016/019426 | 2/2016 |
| WO | WO2016/26053 | 2/2016 |
| WO | WO 16/032875 | 3/2016 |
| WO | WO2016/032875 | 3/2016 |
| WO | WO2016/048800 | 3/2016 |
| WO | WO 2016/012726 | 4/2016 |
| WO | WO2016/094826 | 6/2016 |
| WO | WO2017001851 | 6/2016 |
| WO | WO2016/137347 | 9/2016 |
| WO | WO2016/148675 | 9/2016 |
| WO | WO2016/165030 | 10/2016 |
| WO | WO2017/039596 | 3/2017 |
| WO | WO 17/064719 | 4/2017 |
| WO | WO 17/066518 | 4/2017 |

(56) References Cited

FOREIGN PATENT DOCUMENTS

| WO | WO2017/077356 | 5/2017 |
|---|---|---|
| WO | WO2017/079655 | 5/2017 |
| WO | WO 17/127838 | 7/2017 |
| WO | WO 17/221257 | 12/2017 |
| WO | WO 18/078636 | 5/2018 |
| WO | WO 18/087758 | 5/2018 |
| WO | WO 18/131044 | 7/2018 |
| WO | WO 18/185755 | 10/2018 |
| WO | WO 18/193316 | 10/2018 |
| WO | WO 18/193317 | 10/2018 |
| WO | WO 19/14452 | 1/2019 |

OTHER PUBLICATIONS

International Search Report in PCT Application PCT/IB2014/064586, dated Dec. 23, 2014, in 2 pages.
International Search Report in PCT Application PCT/US2016/060676, dated Nov. 5, 2017 in 7 pages.
International Search Report dated May 11, 2017 issued in corresponding PCT/US2016/060676 (8 pp).
Alam, "Radiological evaluation of lumbar intervertebral instability", Ind J Aerospace Med, 46(2), 2002, 48-53.
Ames, "Impact of spinopelvic alignment on decision making in deformity surgery in adults", J Neurosurg Spine, 2012, 16:547-564.
Breen et al., "An objective spinal motion imaging assessment (OSMIA): reliability, accuracy and exposure data", BMC Musculoskeletal Disorders, 2006, 7(1), (10 pp).
Davis et al., "Measurement Performance of a Computer Assisted Vertebral Motion Analysis System", International Journal of Spine Surgery, 2015, 9(36), (13 pp).
McAfee et al., "The value of computed tomography in thoracolumbar fractures. An analysis of one hundred consecutive cases and a new classification", J Bone Joint Surg Am., 1983, 65-A(4):461-473.
Abe et al. "Scoliosis corrective force estimation from the implanted rod deformation using 3 D FEM analysis", 2015, Scoliosis 10(Suppl 2):52, 6 pages.
Aubin et al. "Preoperative Planning Simulator for Spinal Deformity Surgeries", Spine 2008, 33(20):2143-2152.
Reinshagen et al. "A novel minimally invasive technique for lumbar decompression, realignment, and navigated interbody fusion", J Clin Neurosci. 2015, 22(9):1484-1490; XP055503028.
Rickert et Al., "Posterior lumbar interbody fusion implants", Orthopaede, Springer Verlag, Berlin, DE vol. 44, No. 2 dated Jan. 28, 2015 pp. 162-169.
Spontech Medical AG Vertaplan—die Software für Wirbelsäulenchirurgen, Aug. 29, 2013 Retrieved from the Internet: URL: https://www.youtube.com/watch?v=q0qhW1T1cp8 in 1 page.

\* cited by examiner

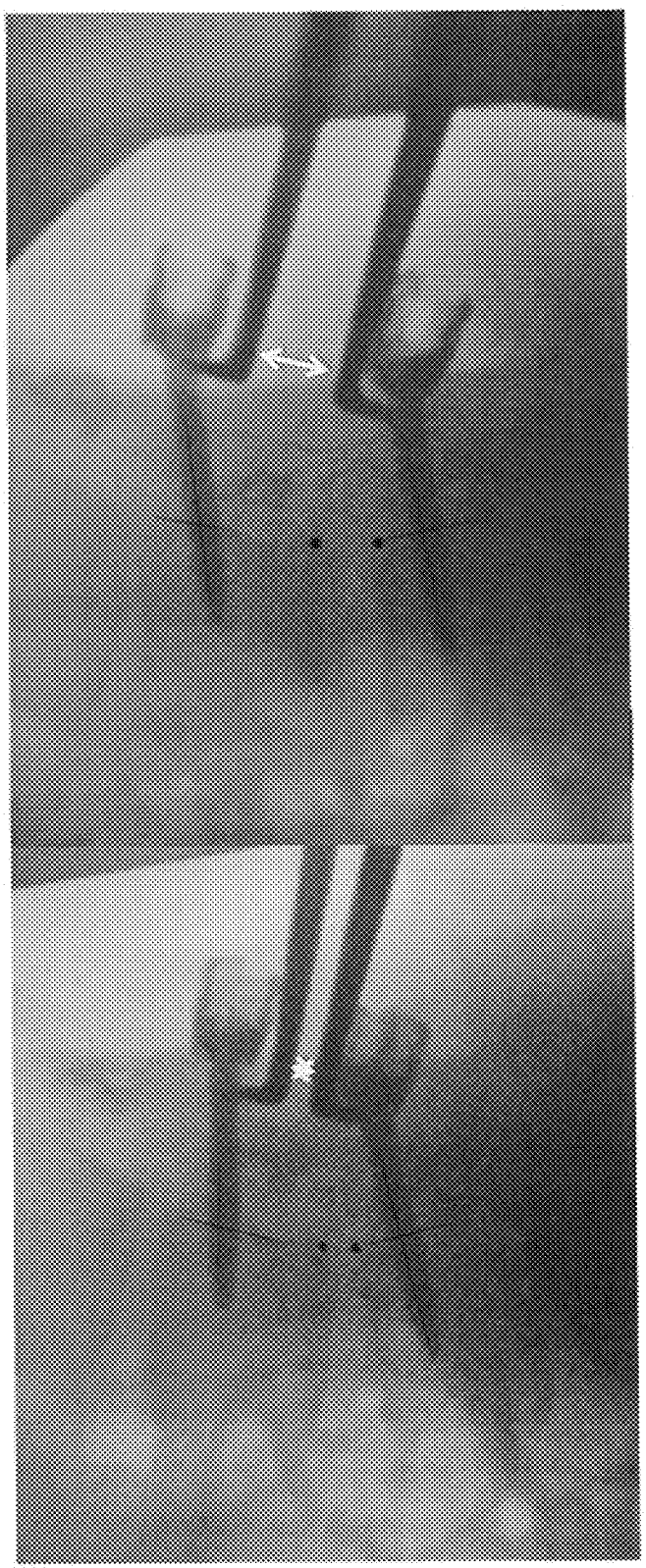

Test Translation and Angulation with "Neutral Zone" type force AFTER the minimum Neurologic Decompression (Diskectomies and osteophytectomies)

METHODS AND APPARATUS FOR SPINAL RECONSTRUCTIVE SURGERY AND MEASURING SPINAL LENGTH AND INTERVERTEBRAL SPACING, TENSION AND ROTATION

CROSS-REFERENCE TO RELATED APPLICATIONS

This application claims the benefit of U.S. Provisional Patent Application Ser. No. 62/250,743 filed Nov. 4, 2015, and U.S. Provisional Patent Application Ser. No. 62/413,159 filed Oct. 26, 2016, both of which are incorporated herein by reference.

FIELD OF THE INVENTION

The present invention relates to methods and apparatus for spinal surgery, and more particularly relates to methods and devices for spinal reconstructive surgery, measuring spinal length and intervertebral spacing at the middle column, measuring intervertebral tension and establishing intervertebral spacer heights, and measuring intervertebral rotation.

BACKGROUND INFORMATION

Spinal reconstructive surgery may be used to correct anterior/posterior sagittal plane (Z-axis) imbalances ranging from abnormal (e.g., 40 mm) to severe (e.g., 90 mm) and/or to correct lateral coronal plane (X-axis) imbalances (e.g., greater than 20 mm). During such reconstructive surgery, vertical spacings between adjacent vertebrae along the length of the spine (Y-axis) may be adjusted using intervertebral spacers, rods, plates and the like.

Current products are not sufficient to provide full three-dimensional spinal re-alignment. The quantitative data provided by conventional instruments concerns the angles, e.g., ISSG parameters such as LL, PI, SS, CSVL or linear measurements in other planes, such as SVL in the sagittal plane and CSVL in the coronal plane. Current techniques do not account for the Y-axis, and the definition of vertical stability along the Y-axis of the human spine has not been adequately established. Surgeons cannot rely on angles alone to restore three-dimensional spine alignment. Additional quantitative measures are needed to ensure neurological preservation and recovery by preventing nerve root stretch during distraction and nerve root impingement/buckling of dura during osteotomy, optimize lordotic/kyphotic expandable cage fit, and optimize neuro-foraminal volume. Other factors that need to be measured are the tension of the posterior longitudinal ligament (PLL) and axial height. However, currently available products do not measure these parameters.

A shortcoming of conventional spinal column measurement techniques along the Y-axis is that overall sagittal alignment guides may be met but intervertebral spacing between a particular set of vertebrae may be severely impaired. For example, a patient may have dramatic over-distraction of two adjacent vertebrae, yet pelvic incidents, pelvic tilt, sacral slope and sagittal vertical alignment may be within a normal range. As another example, extreme shortening may occur at a specific location along the Y-axis of the spine, e.g., caused by a vertebra that is located anterior to an adjacent vertebra, yet sagittal plane SVA, coronal plane CSVL and center sacral vertical line may be within a normal range.

SUMMARY OF THE INVENTION

The present invention provides methods and apparatus for performing spinal reconstructive surgery, including measuring spinal length in the Y-axis at the middle column, measuring intervertebral spacing in the Y-axis at the middle column, measuring intervertebral tension applied to the posterior longitudinal ligament, establishing the height of intervertebral spacers along the Y-axis at the middle column based on one or more of such measurements, measuring intervertebral rotation around the Y-axis, and measuring flexion-extension or anterior-posterior rotation around the X-axis.

An aspect of the present invention is to provide a method of measuring intervertebral spacing length at a middle column of a spine comprising positioning a first middle column marker in a first vertebra within the middle column, positioning a second middle column marker in a second vertebra within the middle column, and measuring a distance between the first and second middle column markers to thereby determine the intervertebral spacing length at the middle column.

Another aspect of the present invention is to provide a method of measuring spinal length at a middle column of a spine comprising identifying the location of the middle column for individual vertebrae along at least a portion of the length of the spine, measuring the length of each of the vertebrae at the middle column, measuring intervertebral lateral offset distances between adjacent vertebrae, and determining an overall spinal length representing a combination of the measured lengths of the vertebrae at the middle column and the measured intervertebral lateral offset distances.

A further aspect of the present invention is to provide a method of measuring intervertebral tension of a spine comprising positioning a first bone anchor in a first vertebra within a middle column of the spine, positioning a second bone anchor in a second vertebra within the middle column of the spine, distracting the first and second vertebrae by applying force against the first and second bone anchors, and measuring tension of a posterior longitudinal ligament between the first and second vertebrae at different distraction distances.

Another aspect of the present invention is to provide a method of spinal reconstructive surgery comprising measuring a pre-operative spinal length at a middle column of the spine, and establishing at least one intervertebral spacing in the spine based on the measured pre-operative spinal length at the middle column.

A further aspect of the present invention is to provide a method for measuring rotational displacement of adjacent vertebrae of a spine comprising positioning a middle column marker in at least two vertebrae of the spine within a middle column of the spine, applying a force between the middle column markers, and measuring relative angular movement between the middle column markers.

Another aspect of the present invention is to provide an apparatus for measuring intervertebral spacing distances between adjacent vertebrae at a middle column of a spine comprising at least two middle column markers positionable in at least two vertebrae within a middle column of the spine, and a detector capable of measuring a distance between the middle column markers at the middle column.

A further aspect of the present invention is to provide a intervertebral tension measuring apparatus for measuring intervertebral tension and identifying intervertebral spacer lengths comprising a distractor engageable with bone anchors installed in adjacent vertebrae within a middle column of a spine, a tension measurement device structured and arranged to measure amounts of force applied by the distractor against the bone anchors when the vertebrae are separated from each other by the distractor against tension applied by a posterior longitudinal ligament of the spine, and a distance correlating device structured and arranged to record varying distances between the adjacent vertebrae in the middle column and correlating each of the varying distances with a force measured by the tension measuring device corresponding to the tension applied by the posterior longitudinal ligament.

An embodiment of the present invention provides a real time measurement guide. Tensioning may be done as maneuvers are performed reducing the spine. Conventional intraoperative fluoroscopy is slightly delayed and after-the-fact, and excessive nerve root traction might already have occurred. Integrated real time three dimensional mapping is provided in accordance with embodiments of the present invention. The middle column measurements may be measured pre-operatively, intraoperatively and/or postoperatively.

Embodiments of the present invention allow the surgeon to measure the actual effect of the cage or spine manipulation on the middle column. Actual middle column height is measured including any changes in middle column height, along with angular changes. The output versus the idealized input may be provided. Conventional computerized mapping programs measure only the idealized introduction, e.g., of an 11 mm cage even though there is subsidence and it only increases the axial height at the middle column 9.5 mm. Subsidence is common as the vertebral bodies are osteoporotic and the cage might sink into the softer bone to some extent. In certain conventional procedures, a 30 degree hyperlordotic cage may yield a correction of 8.5 to 41.1 degrees, which may be an unacceptably wide variation and too unpredictable. Such systems only measure the idealized angles and do not measure the tension or the actual axial spinal height. Variation or unpredictability result from subsidence, inadequate soft tissue release and lack of PLL tension measurement.

Embodiments of the present invention provide precise measurements at the middle column, thereby giving surgeons better guidance. Precise measurements may be integrated into an automated or robotic system. Ligament tension (i.e., PLL) may be used as a gauge for 3D spinal re-alignment/global spinal balance. The MC measurement gauge may ensure that vertebral bone and cage height match up with PLL tension. Benefits increase across multiple levels because small errors can otherwise be compounded across multiple levels. Problems from over/under distraction include: in cervical-chin on chest deformity; in lumbar-flat back syndrome; improper anterior load sharing; and pedicle screw breakage/cage dislodgement/pseudarthrosis. The present invention makes results more reproducible and predictable.

BRIEF DESCRIPTION OF THE DRAWINGS

FIGS. 7 and 8 are spinal images illustrating a middle column measurement and distraction method and apparatus in accordance with an embodiment of the present invention.

DETAILED DESCRIPTION

Figure 1:
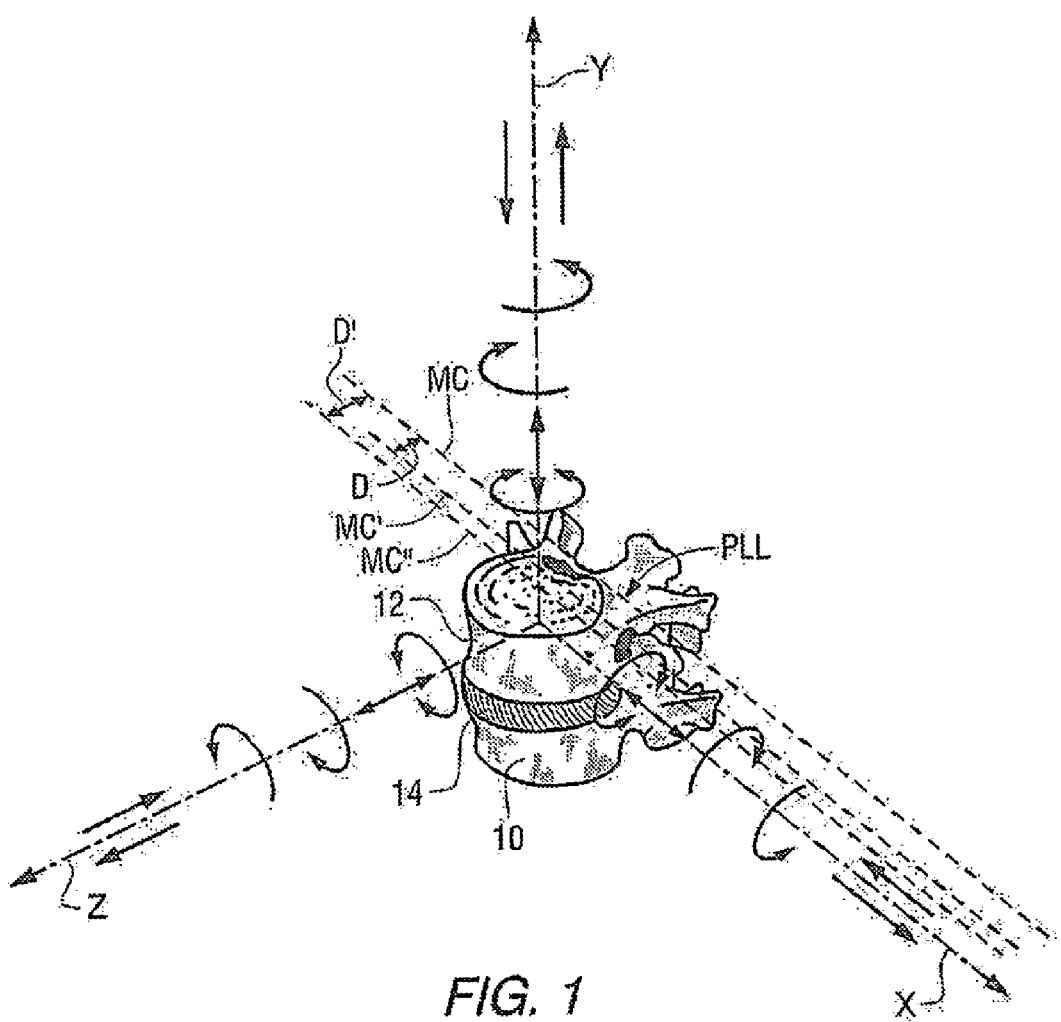
FIG. 1 is an isometric view of spinal vertebrae illustrating the X-axis, Y-axis and Z-axis.

FIG. 1 is an isometric view illustrating two adjacent spinal vertebrae 10 and 12 separated by a spinal disk 14. Three axes have been labeled in FIG. 1, the X-axis, Y-axis, and Z-axis. The X-axis is oriented laterally from side-to-side of the patient. The Y-axis is oriented along the length of the spine. The Z-axis is oriented from front to back of the patient, i.e., the anterior-posterior direction. In accordance with embodiments of the present invention, spinal length along the Y-axis at the middle column may be measured, intervertebral spacing along the Y-axis at the middle column may be measured, intervertebral tension applied to the posterior longitudinal ligament along the Y-axis may be measured, the height of intervertebral spacers along the Y-axis at the middle column may be measured, intervertebral rotation around the Y-axis may be measured, and flexion-extension or anterior-posterior rotation around the X-axis may be measured.

Figure 2:
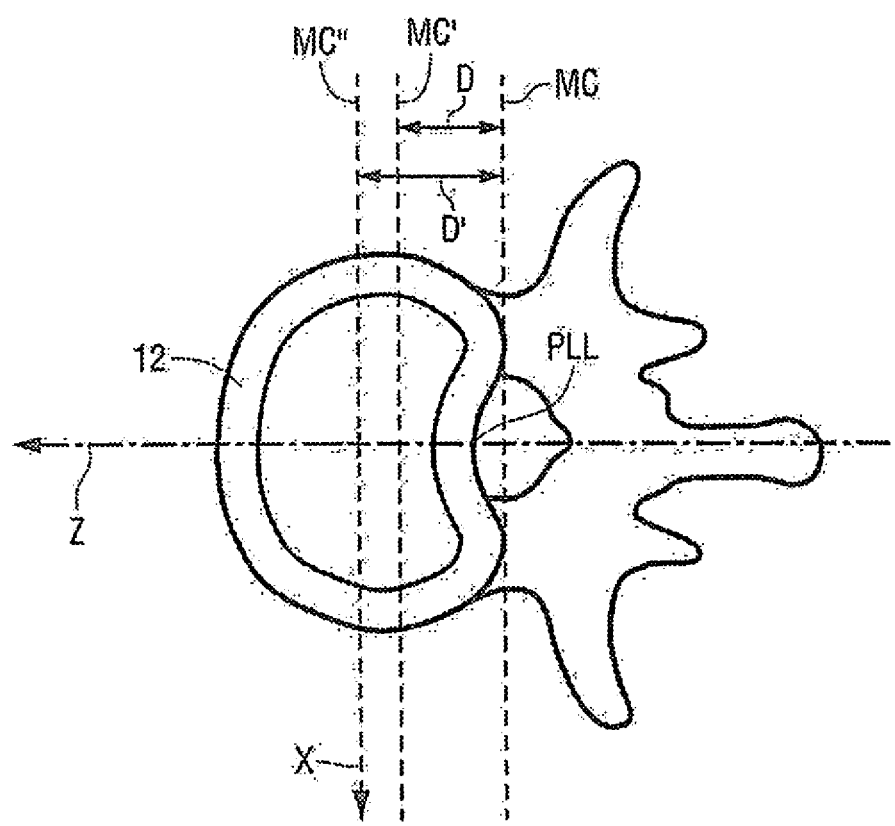
FIG. 2 is a top view of a spinal vertebra illustrating a middle column region thereof.

FIG. 2 is a top view of a spinal vertebra 12 in which the X-axis and Z-axis have been labeled. The body of the vertebra 12 includes a posterior side along which the posterior longitudinal ligament runs (not shown). A point of contact between the posterior side of the vertebral body 12 and the posterior longitudinal ligament is labeled PLL in FIG. 2.

As used herein, the term "middle column" means a region running along the Y-axis of the spine and extending along the Z-axis that is bounded on one side by the posterior surface of each vertebral body in an area near the posterior longitudinal ligaments (PLL), and is bounded on another side (measured along the Z-axis) by a distance substantially one-third of the distance through the vertebral body measured from the posterior surface of the vertebral body in the Z-axis, i.e., from the posterior side to the anterior side of each vertebral body. It is to be understood that the anterior boundary of the middle column is substantially at the one-third distance (33.3 percent), but the anterior boundary may extend up to 50 percent of the distance through the vertebral body measured long the Z-axis, i.e., the middle column may nominally range of from 0 percent to 33.3 percent, but may range up to 50 percent in certain embodiments.

As shown in FIGS. 1 and 2, the posterior and anterior boundaries of the middle column may be defined by lines MC, MC' and MC" separated from each other along the Z-axis. The posterior middle column line MC is located at a position along the Z-axis corresponding to the posterior side of the vertebral body 12 at a location near the posterior longitudinal ligament PLL. The one-third middle column line MC' is spaced from the posterior middle column line MC along the Z-axis a distance equal to one-third of the width of the vertebral body 12, e.g., the one-third middle column line MC' is located 33.3 percent of the distance through the vertebral body 12 measured from the posterior middle column line MC. The one-half middle column line MC" is located 50 percent of the distance through the vertebral body 12 measured from the posterior middle column line MC.

Figure 3:
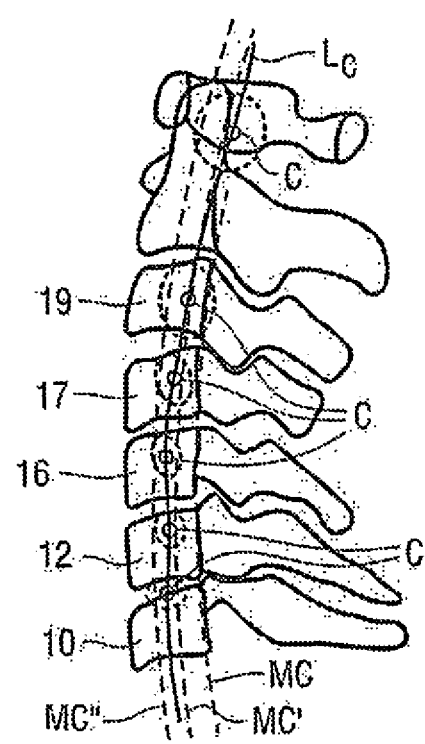
FIG. 3 is a partially schematic side view of a portion of a spine illustrating centers of rotation of the spinal vertebrae.

FIG. 3 is a partially schematic side view of a portion of a spine in which the center of rotation of each vertebra has been indicated with a line connecting the centers of rotation. The spine includes multiple vertebrae 10, 12, 16, 17 and 19, each of which has a center of rotation C around the X-axis for sagittal plane motion. A center of rotation line $L_C$ is shown in FIG. 3 connecting the centers of rotation C of the individual vertebra 10, 12, 16, 17 and 19. FIG. 3 also shows the middle column lines MC, MC' and MC". As can be seen, the centers of rotation C and center of rotation line $L_C$ are located within the middle column.

Figure 4:
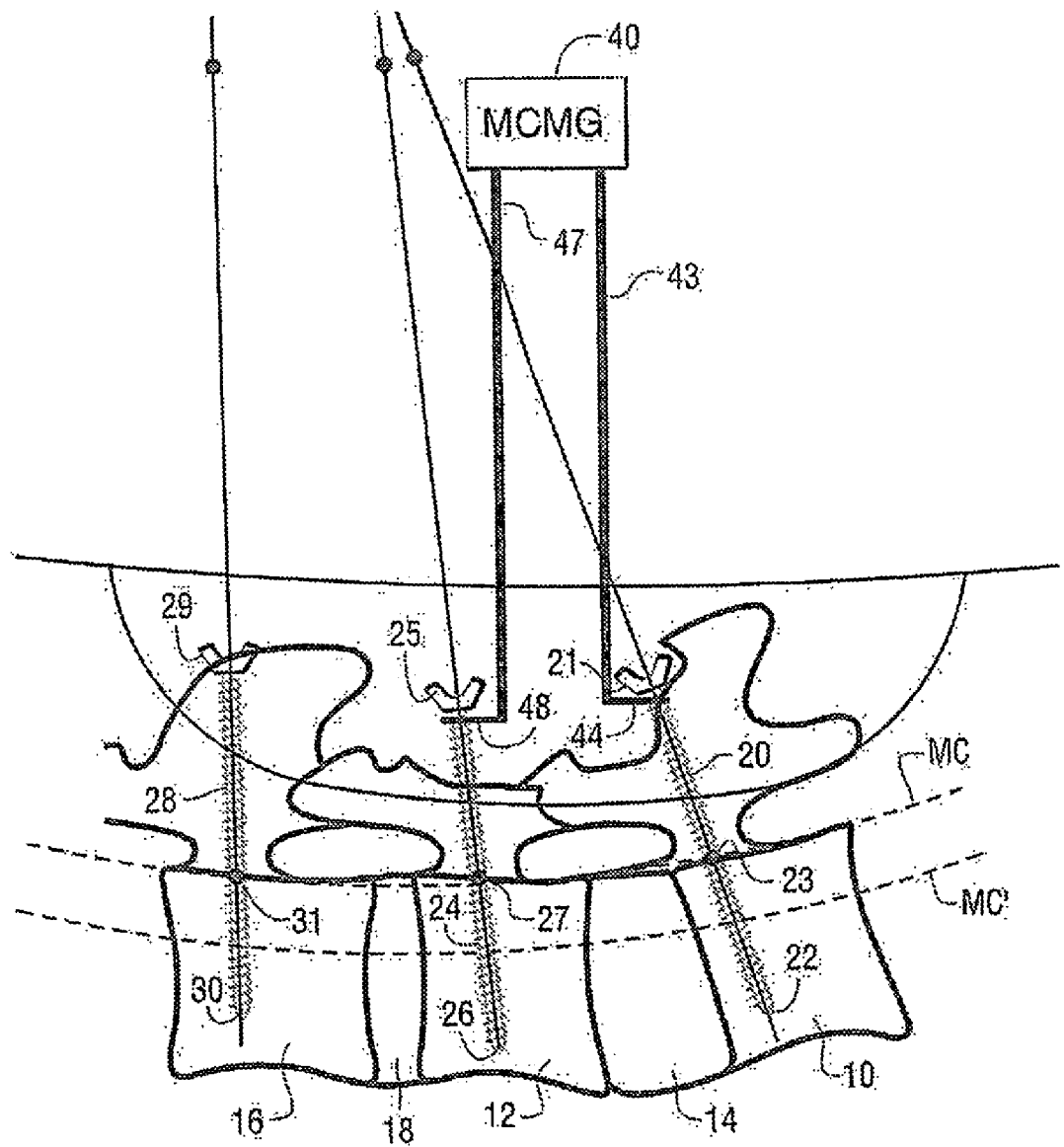
FIG. 4 is a partially schematic side view of a section of a spine illustrating a middle column measurement method and apparatus in accordance with an embodiment of the present invention.

FIG. 4 is a partially schematic side view of a section of a spine including three vertebrae 10, 11 and 16, each of which has a bone anchor in the form of a pedicle screw 20, 24, 28 installed therein. FIG. 4 shows the posterior middle column line MC, and the anterior middle column line MC', which is located at a distance one-third of the diameter of each vertebra, measured from their posterior sides, as described above. The pedicle screw 20 includes a head 21 and tip 22. The pedicle screw 24 includes a head 25 and tip 26. The pedicle screw 28 includes a head 29 and tip 30. As further shown in FIG. 4, each pedicle screw 20, 24 and 28 includes a central column marker 23, 27 and 31 that is located on or near the posterior middle column line MC when the screw is installed in the vertebra. The middle column markers 23, 27 and 31 may comprise any suitable types of detectable feature, such as a shoulder, recess, dissimilar material, or the like. FIG. 4 also schematically shows a distraction device 40 including two distractor arms 43 and 47, each of which is connected near the heads 21 and 25 of the pedicle screws 20 and 24.

A middle column measurement guide or gauge (MCMG) may thus be utilized in a posterior approach to the lumbar spine. Pedicle screws or posted pedicle screws may be used such that the surgeon or operator can use fluoroscopy and determine from the outer silhouette of the screw or other detectable feature exactly the depth of screw insertion to the middle osteoligamentous column where the posterior longitudinal ligament lies in the lateral projection. The screws can be placed in lordosis, kyphosis or alternate angles as long as the depth down to the middle column can be ascertained. In this manner, the stresses, axial height, and rotational position of the middle column can be determined. The user may directly measure the distance and the force of distraction and the forces of compression placed along the middle column. The middle column measurement guide allows surgeons to directly measure the force of correction and the tension of ligamentotaxis along the posterior longitudinal ligament.

Figure 5:
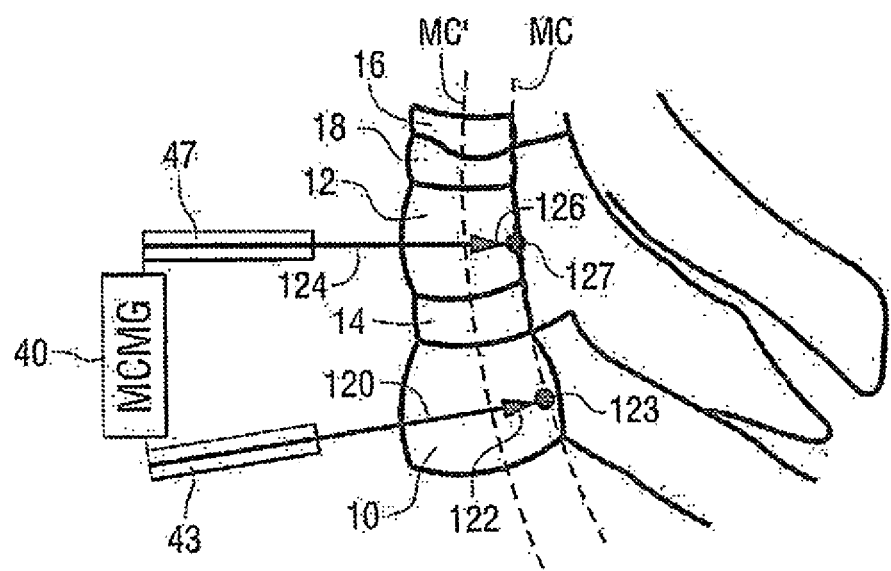
FIG. 5 is a partially schematic side view of a section of a spine illustrating a middle column measurement method and apparatus in accordance with an embodiment of the present invention.

FIG. 5 is a partially schematic side view of a section of a spine in which middle column markers in the form of screws or pins have been installed from an anterior side of each vertebra. A screw or pin 120 having a tip 122 is installed in the vertebra 10, and another screw or pin 124 having a tip 26 is installed in the vertebra 12. The tip 122 of the pin 120 is located at or near a point 123 within the middle column, i.e., at the posterior middle column line MC. The tip 126 of the pin 124 is located at or near a point 127 within the middle column, i.e., at the posterior middle column line MC. A distraction device 40 including distractor arms 43 and 47 attached to the screws or pins 120 and 124 is also schematically shown in FIG. 5.

The embodiment shown in FIG. 5 may use the middle column measurement gauge through Caspar pins which are inserted from the anterior part of the cervical spine, e.g., during anterior cervical discectomy and fusion. The Caspar pins or any rod or anchoring screws placed in the anterior aspect of the cervical vertebral body may be inserted in various neutral or flexion-extension angles to the depth of the middle column. Although the Caspar pins can be placed in lordosis or kyphosis, the tip of each pin may be used as the measuring point lying within the middle column. This configuration of the triaxial quality of middle column measurement guide is advantageous because this makes the anchor points and Caspar pins not dependent on having a parallel or orthogonal orientation with regard to each other. The reference point of three calculated measurements (linear displacement; angular displacement or motion; and strain or stress) may be used to find effective displacements and moments from the tip of the cranial Caspar pin to the tip of the caudal Caspar pin to determine the displacements and moments along the middle column of the spine. The bone anchors can be temporary in order to assess the requirement for a fusion, or they can be permanent anchors intended to be incorporated directly into a fusion instrumentation construct, either minimally invasively, mini-open, or open surgery.

Figure 6:
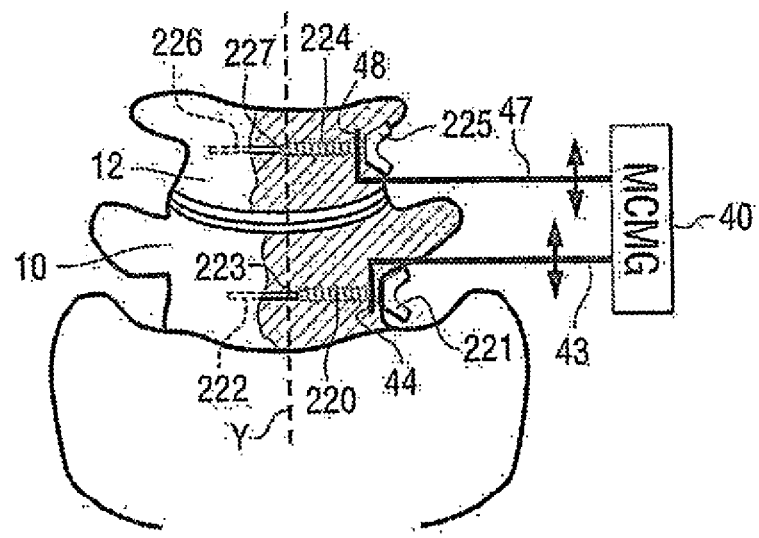
FIG. 6 is a partially schematic front view of a portion of a spine illustrating a middle column measurement method and apparatus in accordance with an embodiment of the present invention.

FIG. 6 is a partially schematic front view of a portion of a spine in which pedicle screws have been installed laterally into each vertebra. A pedicle screw 220 is installed in a vertebra 10. The pedicle screw 220 includes a head 221, tip 222 and transition marker 223. A pedicle screw is installed in another vertebra 12. The pedicle screw 224 includes a head 225, tip 226 and transition marker 227. As schematically shown in FIG. 4, the distraction tool 40 includes one distractor arm 43 attached to the pedicle screw 220 near its head 221, and another distractor arm 47 connected to the pedicle screw 224 near its head 225.

FIG. 6 illustrates a lateral thoracolumbar approach, for example a lateral lumbar interbody fusion LLIF, extreme lateral interbody fusion XLIF, or direct lateral interbody fusion DLIF. Dual diameter screws having shoulders are shown. Even though an operating table may be hinged, and the screws that are placed into the vertebral bodies may be placed at an angle, the middle column parameters can be determined. If a dual diameter screw is used, or a screw that has a marking on the outer silhouette which can be visualized fluroscopically, the depth from the middle column measurement guide down to the middle osteoligamentus column can be accurately determined. This may be used for a lateral lumbar interbody fusion LLIF (DLIF or XLIF) with supplemental fixation. The supplemental fixation may serve a dual purpose—it is also used for compression-distraction of the disc space which is being prepared for the use and implantation of an interbody spacer through a direct lateral approach.

The middle column measurement guide (MCMG) concept can be used for thoracolumbar anterior scoliosis correction. For example, a common screw length is 40 millimeters, therefore a 20 millimeter depth measurement can be placed along a 40 mm screw such that in a typical thoracolumbar curve, where screws are placed from T12-L3, the middle column measurement guide can be used to measure the stresses and forces along the middle column of scoliosis correction at each level—T12-L1, L1-L2, L2-L3. Scoliosis correction may be from T12-L3. The MCMG can be used to calculate the optimal final height of each intervening disk space and the size of interbody spacers to insert in order to correct the scoliotic curvature and create the desired lordosis to achieve an optimal SVL or SVA, sagittal vertical line or sagittal vertical alignment. The MCMG may thus include a three dimensional method used to optimize the final reconstruction orientation of the middle column height in three dimensions along the X, Y and Z-axes and along three anatomic planes (coronal, sagittal, and transverse planes intersecting the middle column of the spine).

FIGS. 7 and 8 illustrate a surgical procedure and associated apparatus for measuring distraction distances between adjacent vertebrae along the Y-axis of a spine at the middle column. FIG. 7 shows an undistracted lumbar vertebrae, while FIG. 8 shows the lumbar vertebrae in a distracted position. As shown in FIG. 7, a line has been drawn along the middle column at the point each pedicle screw passes through the middle column, and dots have been drawn on the edge of each vertebrae at the middle column. The distances between the dots represent the distances between the adjacent vertebrae at the middle column. By comparing the distance between the dots in the non-distracted position (FIG. 7) and the distance between the dots in the distracted position (FIG. 8), the distraction distance is determined to be 5 mm at the middle column in the embodiment shown. An accurate measurement of the distraction distance of the adjacent vertebrae along the Y-axis of the spine at the middle column is thus provided, and can be correlated with the amount of force applied to the distraction tool by the surgeon and the corresponding reaction force applied against the distraction tool by the posterior longitudinal ligament as it is stretched during distraction. For example, the amount of hand tension applied by the surgeon on the distraction tool may be measured qualitatively or quantitatively in order to correlate the distraction distance at the middle column with the applied distraction force. Since the Y-axis distraction distance measured at the middle column in FIGS. 7 and 8 is greater than 3 mm (the distance typically considered to represent instability between adjacent lumbar vertebrae), fusion of the vertebrae is justified in order to provide stability. Embodiments of the invention provide an objective quantitative assessment of the amount of ligamentous laxity between the two vertebra and compares it to a predetermined threshold, whether it be 3 mm distraction tension, 3 mm translation along the Z-axis, 3 mm side-to-side laxity, or the like.

The distance between adjacent vertebrae at the middle column may be measured prior to, during and/or after surgery by any suitable technique, including fluoroscopic techniques in which dots or other markers may be made on fluoroscopic images taken when the vertebrae are undistracted and taken when the vertebrae are distracted. Then the distances between the non-distracted and distracted dots or markers may be compared to determine the amount of movement along the Y-axis of the spine at the middle column. The traditional technique is to measure the amount of subluxation and translation on standing flexion-extension radiographs in the pre-operative state, which is not optimal as the required spinal laminectomy and decompression have not been performed as yet. The present invention allows for an assessment of spinal stability to be performed after the required decompression of neural elements and utilizes skeletal fixation points. The present invention also allows the application of gradations of forces and torques with the spinal musculature in a relaxed or anesthetized state, increasing accuracy. Furthermore, the present invention provides for application of forces through skeletal fixation points which are also more accurate, instead of forces being dissipated through the surrounding spinal soft tissues.

In certain embodiments, each pedicle screw may be provided with a marker or structural feature at the point the pedicle screw intersects the middle column, and the distances between such middle column screw markers or structures may be measured when the vertebrae are undistracted and distracted in order to determine the amount of movement in the y-direction of the spine at the middle column. In another alternative embodiment, a device or extension with a three dimensional array containing L.E.Ds or gyroscopic accelerometers (such as three gyroscopic accelerometers placed perpendicular to each other along each of the X-axis, Y-axis, and Z-axis) may be attached on or near the head of each pedicle screw that can detect relative translational and/or angular movement of the heads of the pedicle screws, and correlate such relative movements of the pedicle screw heads with corresponding relative movement between the pedicle screws at the points they intersect the middle column. Such a device may be mechanically connected between the heads of the pedicle screws to geometrically constrain the device and/or the device may measure relative movement between the heads of the pedicle screws by other means such as laser measurement techniques and the like.

The ability to measure distraction distances along the Y-axis of the spine at the middle column as shown in FIGS. 7 and 8 represents a significant improvement in comparison with conventional techniques that measure displacement of a distraction device, for example, the displacement distance of the handle of a distraction device. While such conventional measurement techniques may provide an accurate measurement of the displacement distance between the heads of adjacent pedicle screws, they do not provide an accurate measurement of the displacement distance between the adjacent vertebrae at the middle column. Specifically, as shown in FIGS. 7 and 8, the distraction instrument located near the head of each pedicle screw moves a distance of 12 mm between the undistracted position (FIG. 7) and the distracted position (FIG. 8). However, the distraction distance at the middle column is actually 5 mm, as determined by the difference between the middle column markers in the distracted position of FIG. 8 and the middle column markers in the undistracted position of FIG. 7. Furthermore there is additional error introduced into conventional measuring techniques as the angle of pedicle screw or marking anchor insertion is quite variable. The present invention provides a core reference to measure vertical spinal height in relation to angular changes and reductions in alignment.

Figure 9:
FIGS. 9 and 10 are spinal images illustrating middle column measurement and distraction methods and apparatus in accordance with an embodiment of the present invention.
Figure 10:
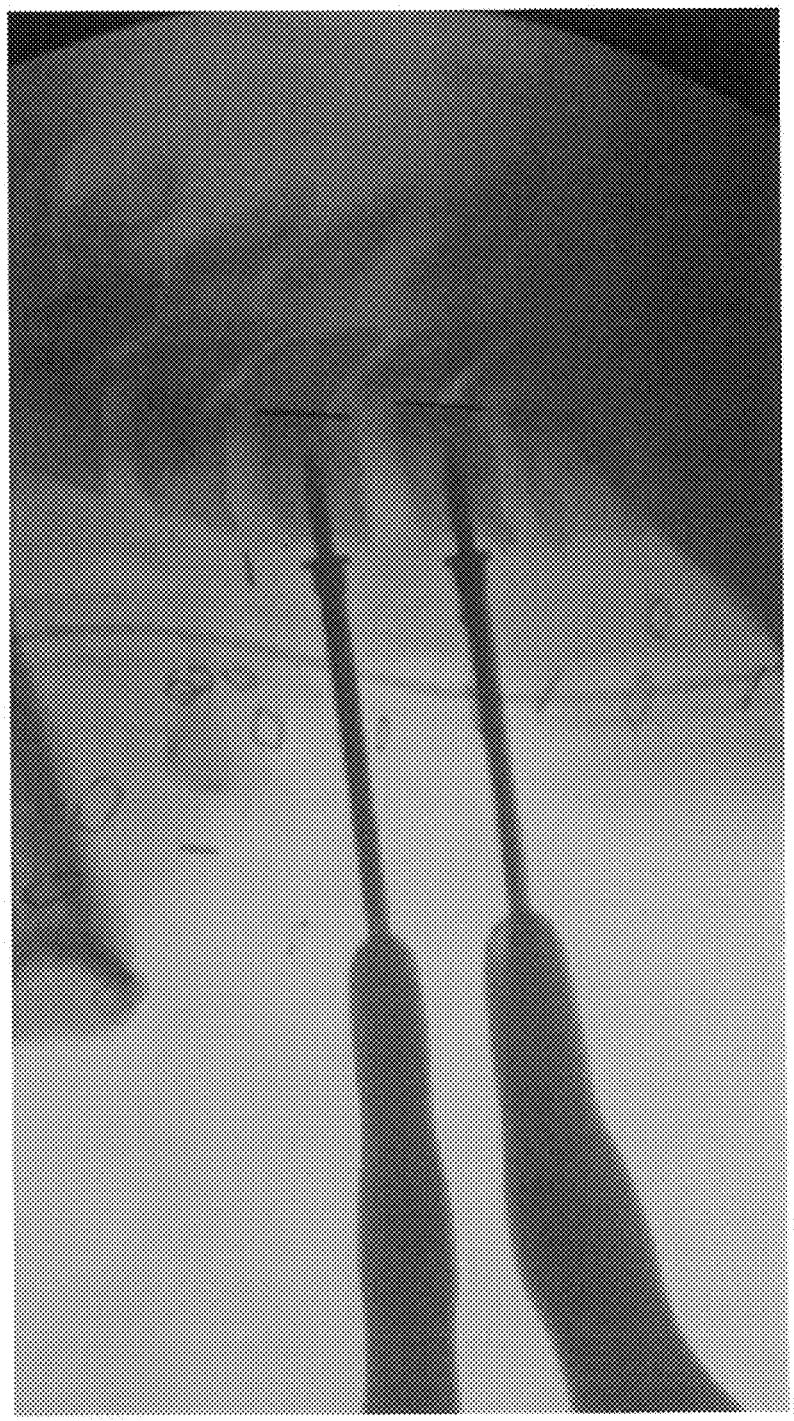

FIGS. 9 and 10 illustrate another method and device in accordance with an embodiment of the present invention in which movement of adjacent vertebrae in the Z-axis is measured at the middle column. In FIGS. 9 and 10, two adjacent vertebrae in the neck or cervical spine of a patient are moved to different relative positions along the Z-axis of the spine, e.g., adjacent vertebrae are pulled forward or pushed back with respect to each other along the Z-axis. Each vertebra is marked with a line located at the middle column. In FIG. 9, the upper cervical vertebrae is positioned rearwardly (posteriorly) of the lower vertebrae, as measured at the middle column of each vertebrae. In FIG. 10, the upper vertebrae is positioned forwardly (anteriorly) of the lower vertebrae, as measured at the middle column. The offset distance in the Z-axis of the spine measured at the middle column is greater than 3.5 mm, indicating an unstable condition that justifies fusion of the adjacent vertebrae in order to stabilize that region of the spine.

The device shown in FIGS. 9 and 10 for translating the adjacent vertebrae in the Z-direction relative to each other may include a rod attached to a Caspar pin through an anterior approach in the cervical spine, (or the head of a pedicle screw in the lumbar spine through a posterior approach) and an arm connected to the rod. By pushing or pulling the arms and respective rods in relation to each other, relative movement of the vertebrae in the Z-axis of the spine is achieved. The amount of force applied to the arms and rods may be measured quantitatively or qualitatively in order to correlate the amount of applied force with the Z-axis offset distance of the adjacent vertebrae at the middle column.

An embodiment of a device that applies a known anterior-posterior force to the upper screw may have three requirements. First it may have a slot or a sliding member to accommodate the varying pedicle-to-pedicle distances. In other words the instrument is able to elongate between the pedicle screw extensions. The slot in the device may accommodate the varying angulations between the two pedicle screw extensions, i.e., the different angles of lordosis and kyphosis between the extensions depending on which vertebral levels are being measured. Secondly, the apparatus may have a constrained attachment or anchorage to the lower pedicle screw or vertebral bone anchor. A stable platform may be provided such that a known force can be applied in a piston-like fashion to the uppermost screw. Thirdly, there may be a gear or teeth along the uppermost screw attachment in order to apply a torque screwdriver or torque-wrench from the side to cause the uppermost screw to be moved in a push-pull direction.

In accordance with certain embodiments, forces applied are in a neutral zone of spinal ligament magnitude with a low physiologic magnitude that will not deform the ligament. Whether the applied force or torque is applied in an X-axis, Z-axis, or Y-axis direction it should be within low physiologic limits that take account of spinal instability. An embodiment may be to apply a stepwise force in a cyclical manner. The cycling of an increasing force application may tend to visually highlight the severity of ligamentous laxity and/or stability. For the posterior longitudinal ligament only a small physiologic force within the neutral zone may be applied. If the spine then demonstrates displacement above 3 mm in the lumbar spine and 3.5 mm in the cervical spine in an anterior-posterior direction, then this may demonstrate spinal instability and the need for fusion. If an applied force is of excessive magnitude such that it is greater than the neutral zone, then this may be an inconclusive demonstration, e.g., instability may or may not be present since an amount of force or torque has been applied which is super-physiologic.

Figure 11:
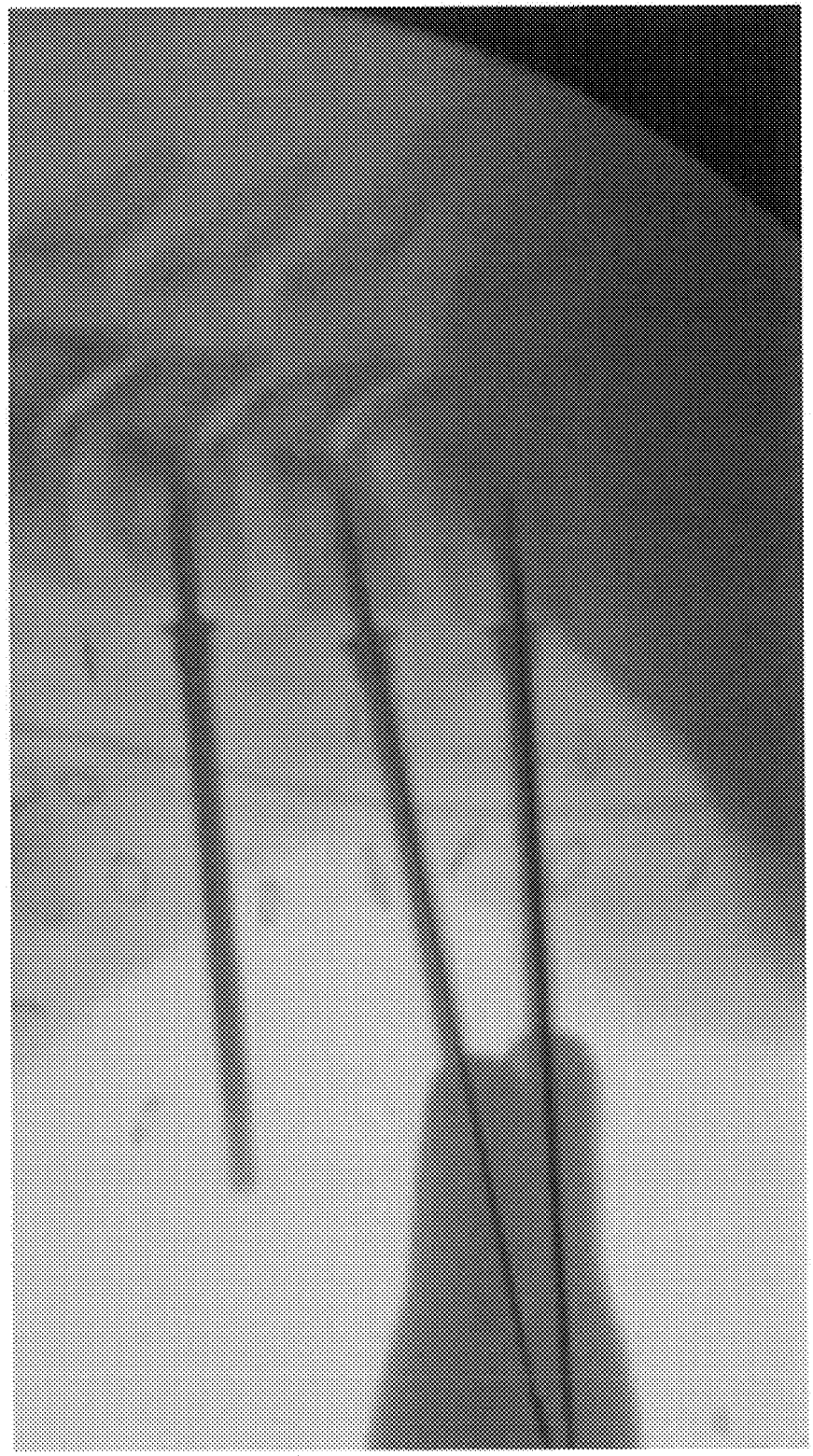
FIGS. 11 and 12 are spinal images illustrating middle column measurement and distraction methods and apparatus in accordance with an embodiment of the present invention.
Figure 12:
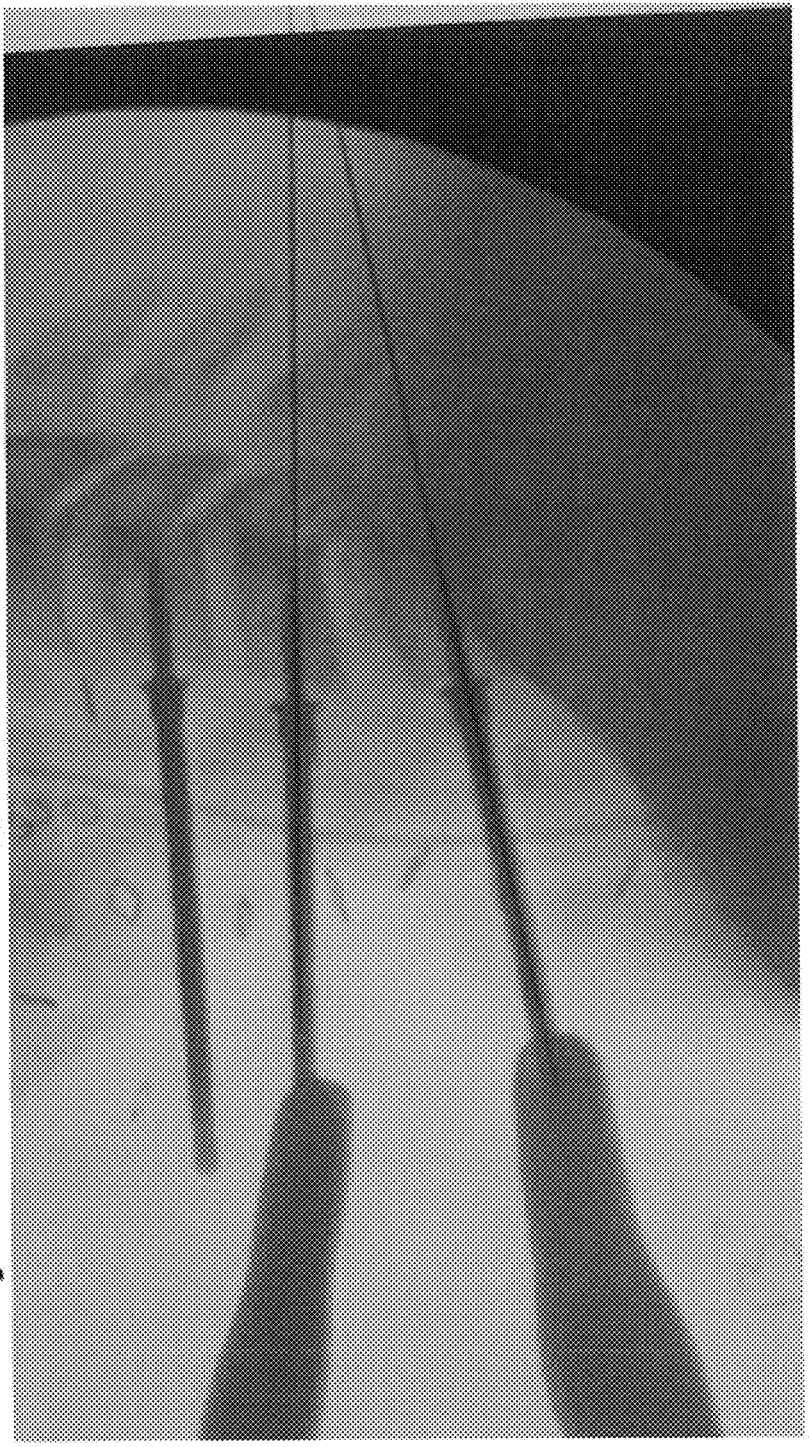

FIGS. 11 and 12 illustrate another method and apparatus in accordance with an embodiment of the present invention in which relative angular movement between adjacent vertebrae is measured at the middle column. In FIG. 11, the angle of Caspar pins placed from an anterior approach in the cervical spine, as measured along the longitudinal axis of each temporary pin, is −13°. In FIG. 12, the angle is +8°. Accordingly, the total angular movement between FIGS. 11 and 12 is 21°, which is well above the threshold angular movement of 11° that would justify fusing the vertebrae together. The device used to generate the relative angular movement may include a rod attached to each of the Caspar pins in the cervical spine (or the head of each pedicle screw and a corresponding control arm in the lumbar spine). The force applied to the arms may be measured quantitatively or qualitatively, and correlated with the measured angular displacement of the vertebrae.

An application of the middle column gap balancing and ligament tensioning device is to measure and apply loads to the spine after spinal decompression surgery. Other techniques such as standing flexion-extension radiographs and measuring the differential stability between pre-operative supine MRI and upright standing radiographs are all assessing the spinal stability while the nerves are still stenotic or compressed. A major advantage of intraoperative MCGB and ligamentous tensioning is that the remaining stability and ligamentous spinal laxity can be assessed after spinal decompression. There are various anatomic structures that may need to be removed depending on the location and severity of spinal cord and/or spinal nerve root compression. Diskectomy, laminotomy, laminectomy, medial facetectomy, total facetectomy, foramenotomy, extraforaminal decompression are procedures that may be required to restore normal neurologic function. Depending on the pre-operative imaging studies the following anatomic structures may have to be removed, resected, or compromised in order to restore neurologic function and/or alleviate pain. The structures include the spinous processes, lamina, facet capsules, facet joint, intervertebral disk, posterior longitudinal ligament, superior articular process, inferior articular process, and ligamentum flavum. An application of the present invention is to provide stability testing can be performed intraoperatively after preforming the neural decompressive part of the surgical procedure. Such tensioning and examination of ligamentous laxity after decompression can lead to a more accurate determination of the requirement for spinal fusion, arthrodesis, stabilization, and/or instrumentation.

Figure 13:
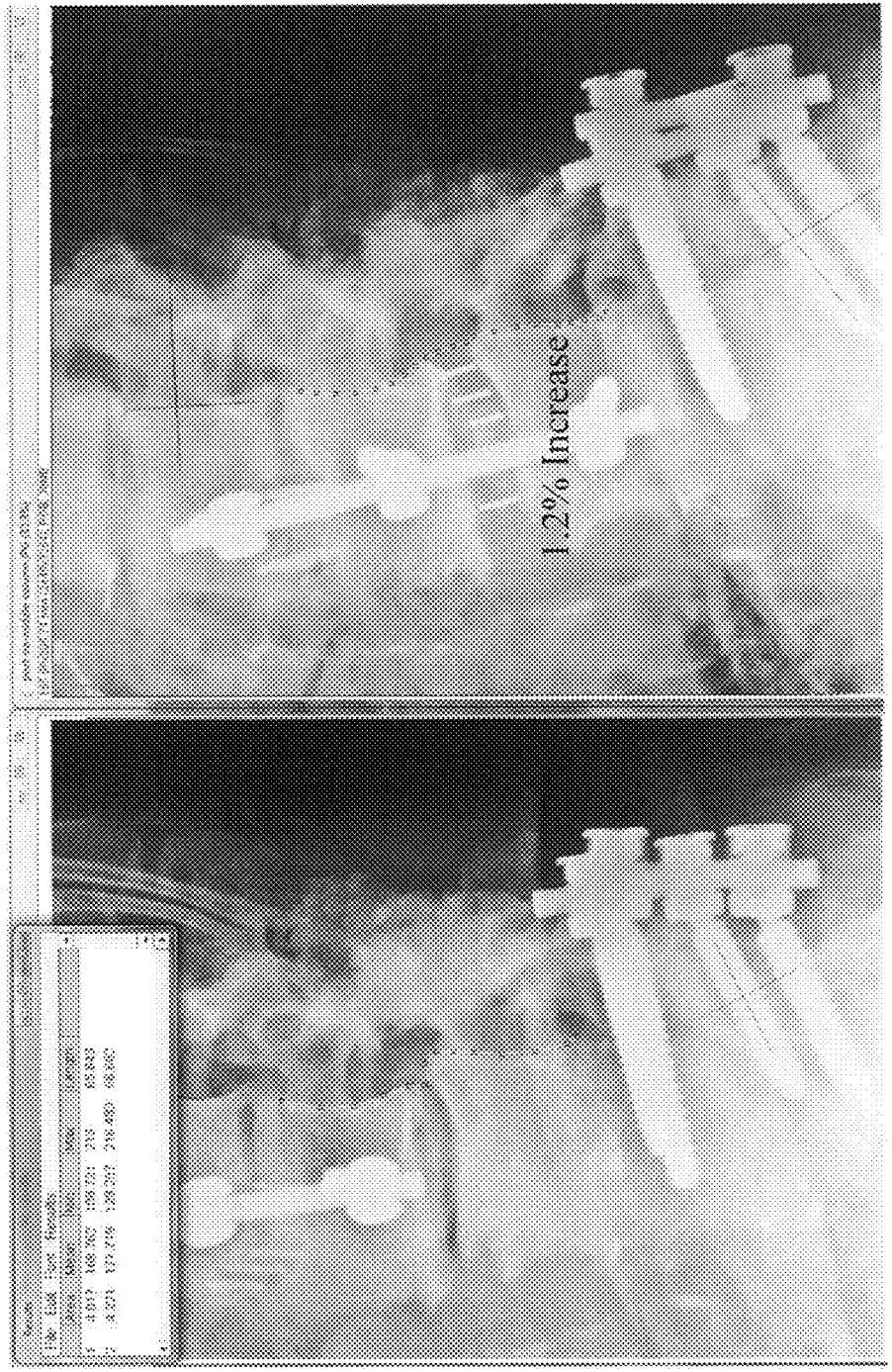
FIGS. 13-15 include spinal images illustrating middle column measurement methods in accordance with embodiments of the present invention.

FIG. 13 describes and illustrates aspects of the present invention. A line is drawn along the posterior side of each vertebra near the normal contact point of the PLL. In the pre-operative condition shown on the left, the intervertebral spacing is 6.58 cm. In the post-operative condition shown on the right, the intervertebral spacing is 6.66 cm, a 1.2 percent increase.

Figure 14:
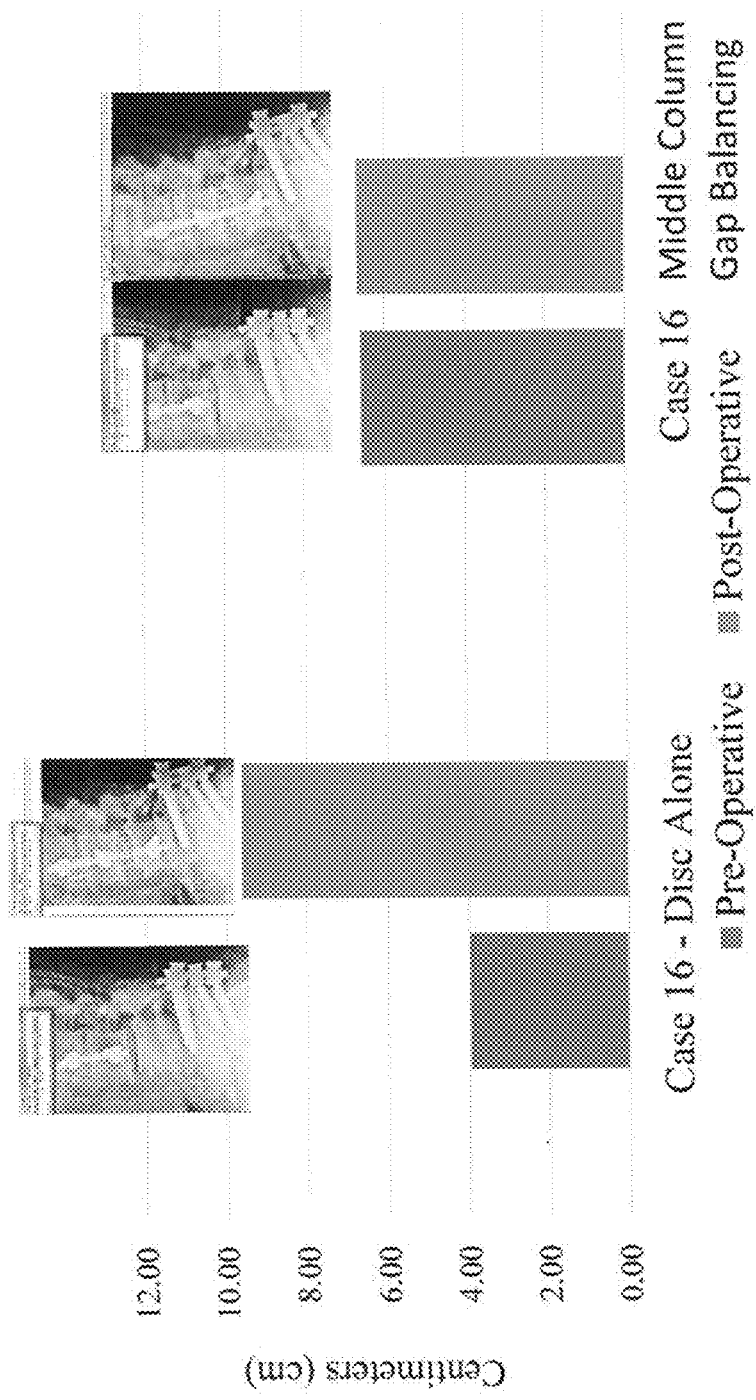

FIG. 14 illustrates pre-operative and post-operative results from a conventional intervertebral spacing measurement technique and a middle column height measurement technique in accordance with an embodiment of the present invention. On the left side, the disk space height is measured with a cage tool, resulting in significant pre-operative and post-operative measurement differences. On the right side, middle column balancing of the present invention is used to determine pre-operative and post-operative intervertebral spacing in an accurate and predictive manner.

Figure 15:
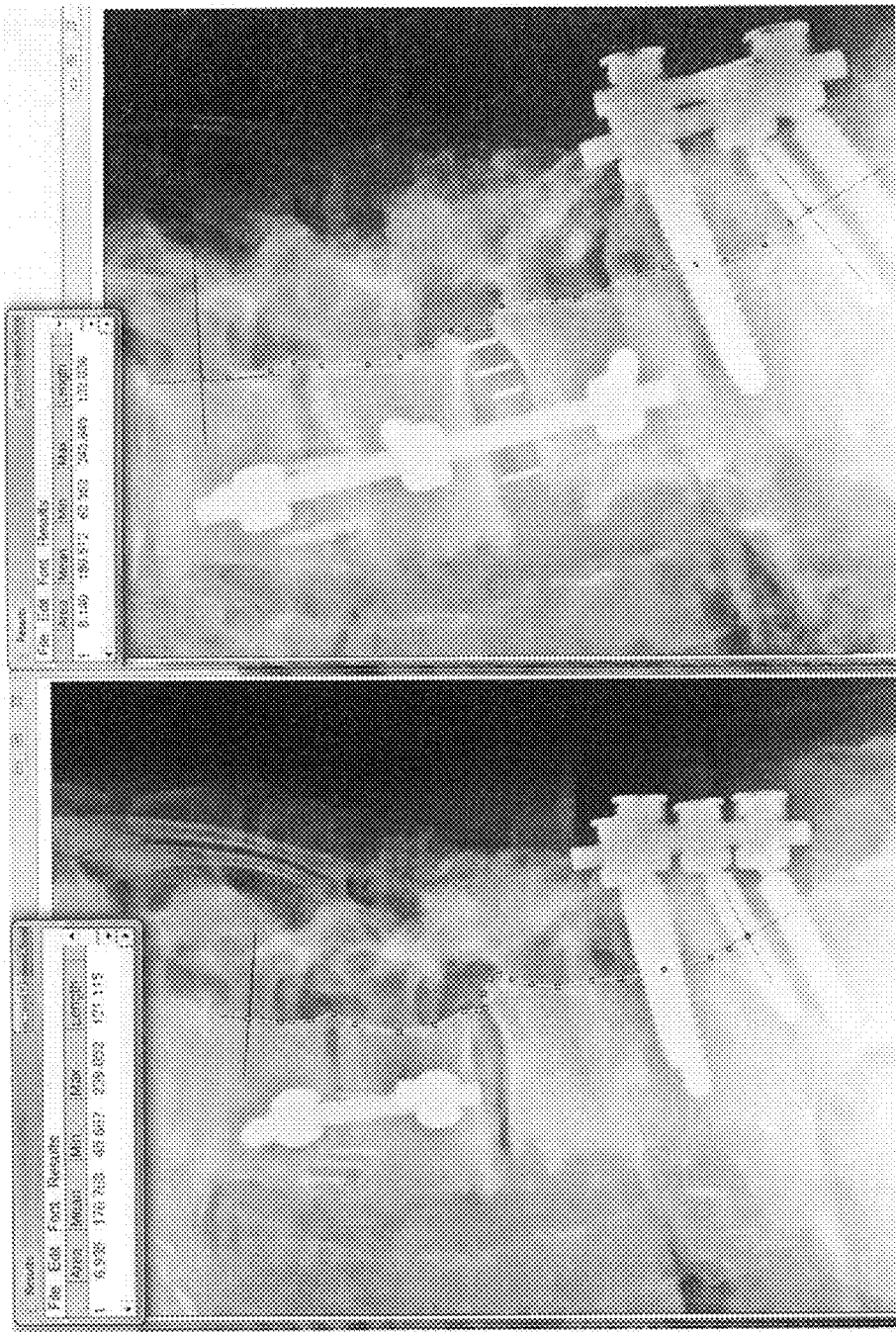

FIG. 15 shows multi-level measurement accuracy over the aggregate of four vertebrae in accordance with an embodiment of the invention. A line is drawn along the posterior side of each vertebra at the normal contact point of the PLL. In the pre-operative condition shown on the left, the aggregated vertebral distance is 12.11 cm. In the post-operative condition shown on the right, the aggregated vertebral distance is 13.20 cm.

In accordance with embodiments of the present invention, instruments are provided for distracting, tensioning and/or translating spinal segments. The instruments can be manual, electrical, or powered by compressed air. The system provides the ability to calculate and quantify the force, displacement and stiffness in the determination of the presence or absence of spinal instability. For example, in the lumbar spine, this may be distraction, translation, or side-to-side ligamentous laxity of 3 mm or more. There can be also excessive angular motion of greater than 11 degrees. The instrument may be used to detect excessive physiologic relationships between the two vertebral segments. The distraction instrument may include a piston parallel to the middle column to measure distraction and compression. A piston perpendicular to the bone anchor may also be provided in order to measure translation (front-back, anterior-posterior) or shear motion.

In accordance with embodiments of the invention, distraction tools such as those described in U.S. Provisional Application Ser. No. 62/413,186 to Paul McAfee and Lukas Eisermann entitled "Apparatus for Spinal Reconstructive Surgery, Measuring Spinal Length and Intervertebral Spacing at the Middle Column, Measuring Intervertebral Tension and Establishing Intervertebral Spacer Heights" filed on Oct. 26, 2016, which is incorporated herein by reference, may be used to perform surgical procedures as described herein.

Figure 16:
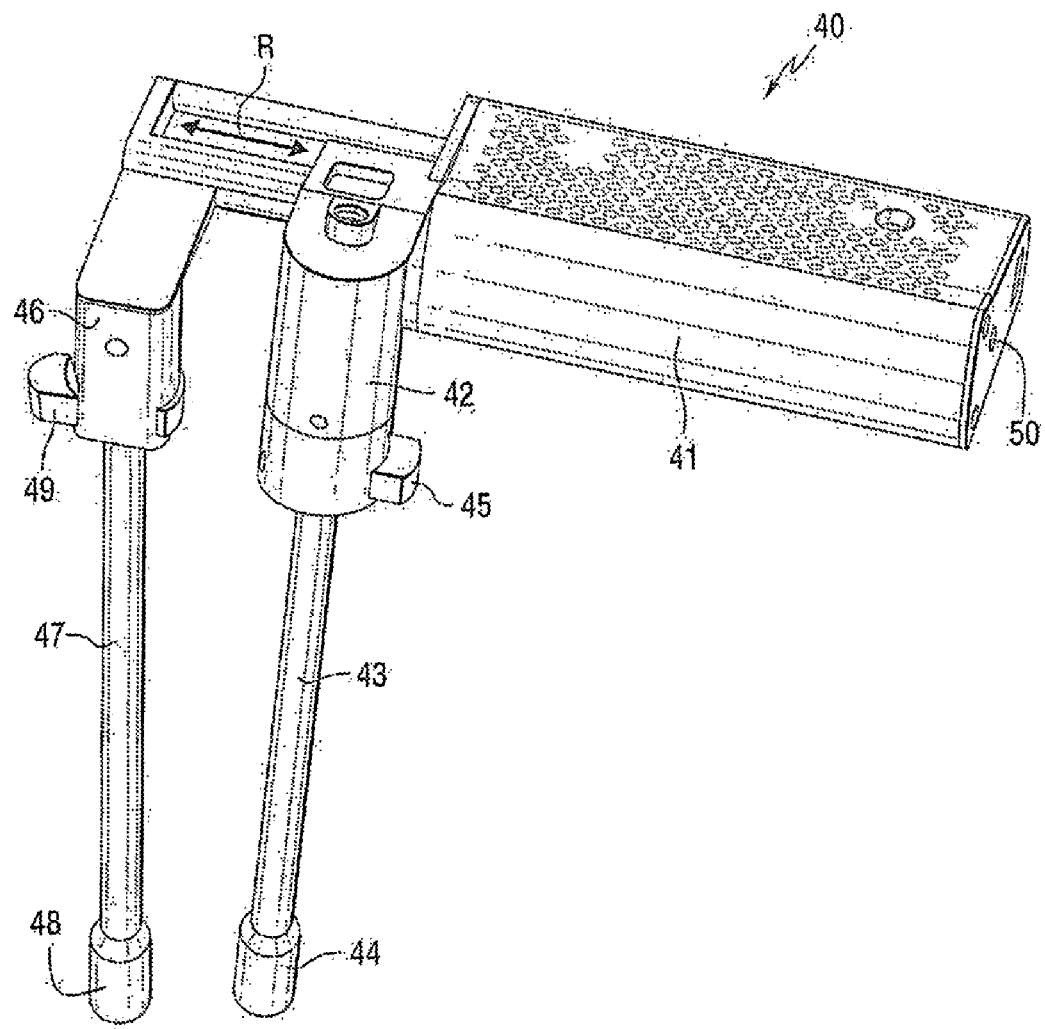
FIG. 16 is an isometric view of a distraction tool that may be used to perform various middle column measurement and distraction methods in accordance with embodiments of the present invention.

FIG. 16 is an isometric view of a distraction tool 40 that may be used in accordance with embodiments of the present invention. The distraction tool 40 includes a body 41 having a pneumatic cylinder located therein. A first distractor arm mounting assembly 42 attached to the housing 41 has a first distractor arm 43 releasably mounted thereon. The distractor arm 43 includes an engagement tip 44 that can be releasably secured to or contact a pedicle screw or pin, as described above. A locking mechanism 45 may be used to releasably secure the distractor arm 43 in the distractor arm mounting assembly 42. A second distractor arm mounting assembly 46 is slidably mounted in relation to the housing 41, and is capable of reciprocating movement R with respect to the housing 41. A second distractor arm 47 is releasably mounted on the second arm mounting assembly 46. The second distractor arm 47 includes an engagement tip 48 that can be releasably secured to or contact another pedicle screw or pin, as described above. A locking mechanism 49 may be used to releasably secure the second distractor arm 47 in the second distractor arm mounting assembly 46. The second distractor arm assembly 46 is mounted on a piston that moves within the pneumatic cylinder in the housing 41. A source of pressurized air (not shown) may be connected to the pneumatic cylinder via a port 50. Delivery of air at controlled pressures causes the first and second distractor arms 43 and 47 to move in relation to each other.

The distraction tool 40 includes opposing distractor arms 43 and 47 that may engage with the pedicle screws 20 and 24 attached to the adjacent spinal vertebrae 10 and 12 as shown in FIG. 4, as well as the screws and pins shown in FIGS. 5 and 6. The distractor arms 43 and 47 are forced away from each other through the use of the pneumatic piston in the housing 41. The pneumatic piston forces the distractor arms 43 and 47 away from each other to thereby increase the spacing between the adjacent vertebrae 10 and 12, e.g., along the Y-axis of the spine. The amount of air pressure applied to the piston controls the amount of distraction. The distraction distance at the middle column may be measured, and correlated with the amount of force applied by the distraction tool 40.

A basic mechanical function of the distraction tool 40 is to apply force to the spine. This may be achieved by using one or more pneumatic pistons. The piston(s) apply constant, predictable force based on the air pressure inside the chamber. This force can be calculated based on the geometry of the piston and/or it may be measured and calibrated based on measuring the force generated by the piston and plotted vs. the input pressure in the piston. A microcontroller can be programmed to correct for any sort of input-output curve correction that may be required to accommodate deviations from the expected linear conversion curve.

By utilizing various combinations of pistons, the spine can be manipulated in either isolated or complex motion planes. An embodiment may utilize one piston to apply force in the axial direction of the spine along the Y-axis. This is the primary motion utilized for middle column balancing, and also the primary motion employed during surgery to distract the disc space.

The distraction tool 40 may be utilized to perform the middle column gap balancing procedure described herein. For example, based on a pre-operative fluoroscopy scan, the spinal length at the middle column is measured, and then the target axial distraction distance is calculated based on restoring the spine to its natural anatomic position, e.g., when the PLL is straightened and tensioned. Either by applying a known force and monitoring progress by fluoroscopy, or by providing the target distance to the microcontroller and allowing the distraction tool to apply force as needed, the target may be reached. To ensure that the procedure is performed safely, upper limits of force and distraction distance may be programmed into the control software. These limits may also be physically designed into the tool by means of pressure release valves that actuate above a certain air pressure and/or mechanical stops to prevent excess motion. Both air pressure limits and mechanical stops could be fixed in manufacturing, or could be provided as features adjustable by the surgeon.

The force and resulting motion achieved may be plotted on a force-displacement graph. This graph can be used to assess the degree of stability in the spine. For example, a current medical guideline suggests that a spinal motion segment which moves 3 mm or more on flexion-extension x-ray analysis should be fixated by spinal fusion, whereas a spinal motion segment moving less than this should not be fused. Distraction instruments can apply the force necessary to move the spine in an objective, controlled manner, while simultaneously recording the resultant motion.

Additionally, by attaching a communications means, such as a Bluetooth chip, an Ethernet card, or other means of exporting a digital signal, to the microcontroller, the instrument is capable of sending the information gathered to a storage device. The storage device may be any form of computer memory, memory attached to an electronic device such as a printer, or may be uploaded to a database on the internet. The information can then be utilized as part of an electronic record of the surgery. It may be a standalone record or may be combined with the outputs of other devices used during the surgery, such as the anesthetic record.

A basic control loop may include the steps of: read data from pressure sensor; compare to pressure level to command input level; convert pressure to force; adjust signal to digital pressure regulator to increase or decrease the amount of pressured allowed by input valve; read a sensor such as a touchless motion sensor or mechanical control button; and interpret sensor information to increase or decrease command pressure.

A middle column gap balance control loop may include the steps of: input target distraction distance; command pressure to increase by a defined step; compare pressure command to maximum allowed pressure; if pressure command is less than maximum allowed pressure, increase pressure; if not, exit loop; read displacement data; compare displacement data to maximum allowed displacement data; if less than maximum displacement, proceed; if not, exit loop; if displacement data is less than target distance, continue; if not, exit loop.

The target distraction distance may be input as a numerical value by the surgeon, or it may be input via software means based on image analysis of the middle column distance. If the target distance is determined by image analysis, then that image analysis can be updated iteratively as new fluoroscopy images are made, allowing continually improving accuracy.

In accordance with other embodiments of the present invention, rotational displacement of adjacent vertebrae may be measured including axial rotation around the Y-axis (IVR, intervertebral rotation) and/or flexion-extension around the X-axis (anterior-posterior rotation). Such rotational displacement measurements may be made during surgical approaches from the side of the patient's spine in certain embodiments. During such procedures, a screw or pin may be inserted at the side of each vertebra in the middle column, e.g., at the instantaneous axis of rotation (IAR) located one-third of the distance from the posterior edge of the vertebrae and two-thirds of the distance from the anterior edge of the vertebrae. The laterally extending pins in the adjacent vertebrae may be manipulated to rotate the adjacent vertebrae with respect to each other in the Y-axis and/or the X-axis. For example, a hydraulic or pneumatic piston may be used to apply a selected amount of force against the laterally extending pins in order to cause rotational displacement around the Y-axis and/or X-axis.

In certain embodiments, rotational displacement may be measured prior to a surgeon's procedure in the disk space between the adjacent vertebrae, and after such a procedure, in order to accurately measure the pre-operative rotational displacement(s) and the post-operative rotational displacement(s) to determine rotational instabilities pre- and post-operatively. For example, if a pre-operative rotational displacement at a given force level is 10 degrees pre-operatively, and the angular displacement at the same force level is 20 degrees post-operatively, such a significant increase in rotational displacement may signify a sufficient amount of rotational instability that would warrant an intervertebral fusion procedure in order to reduce or eliminate the measured rotational instability.

In certain embodiments, when rotational displacement around the Y-axis is measured, the displacement tool may be connected between the two pins attached to the adjacent vertebrae, and the tool is used to move the pins with respect to each other to different angular positions around the Y-axis. Intervertebral rotation is a term describing axial rotation, clockwise and or counterclockwise, around the Y-axis. The range of upper limit of normal physiologic motion may be a range of 15 to 22 degrees.

In the embodiment where rotational displacement is measured around the X-axis, the displacement tool may be used to force the pins to move with respect to each other in the anterior/posterior direction, which causes flexion/extension and rotation around the X-axis. A straight or linear anterior-posterior displacement along the Z-axis can be referred to as IVT or intervertebral translation. IVT usually refers to anterior-posterior linear displacement along the Z-axis. The upper limit of physiologic IVT may be approximately 3 mm in the lumbar spine and 3.5 mm in the cervical spine. The amount of rotation around the X-axis may be measured or calculated via the rotational displacement tool itself, or may be measured by conventional techniques such as fluoroscopy or the like. It can also be measured using quantitative motion analysis computer programs. As discussed above, the laterally extending pins may be positioned within the middle column at the instantaneous axis of rotation (IAR). The angular displacement around the X-axis may be measured directly by tracking angular movement of one pin using the other pin as a reference or base point. Alternatively, angular displacement around the X-axis may be determined by measuring anterior/posterior translational movement of one pin with respect to the other along the Z-axis (intervertebral translation, IVT), and correlating such translational movement with a corresponding rotational movement (Flexion and Extension).

Embodiments of the invention allow measurement of IVR and IVT through a direct lateral approach to the spine, before and after spinal decompression, discectomy, and/or bone removal (necessary for optimal neurologic function). Two pins, screws, or skeletal fixation points may be inserted in the side of the adjacent vertebral segments, minimally invasively, percutaneously, or open surgically to provide calculation and measurement of IVR, IVT, rotation and or linear displacement of the X, Y or Z-axis.

In accordance with embodiments of the invention, a referencing system for the spine may be provided with anchors placed with accelerometers, trispiral goniometers, and linear measurement sensors that can be used to determine the change in height or angle of the vertebral orientation, the center of rotation of the functional spinal units or to define the normal tolerances of spinal stability. The referencing system may utilize anchors attached to the middle column segmentally, each vertebrae may have an anchor with an array that can be picked up via a sensor placed for example at the PSIS, posterior superior iliac spine portion of the pelvis. A MEMS system may be used. The linear and angular changes with tensioning or a known moment can be used to make a determination as to whether the spinal segment with the anchor is stable or not. A database may establish normal stable conditions, e.g., by attaching electronic goniometers, accelerometers and/or extensometers to percutaneously placed pedicle screws with the marks placed at the depth of the junction of the pedicle base and the middle column.

The criterion for stability in the Y-axis may be more exacting than the X-axis or the Z-axis. For example, the threshold for health related quality of life measurements (HRQOL) deterioration is >40 mm in the sagittal plane and >20 mm in the coronal plane (scoliosis which is out of balance). In the Y-axis it may be on the order of 3.5 mm in the cervical spine, greater than 2 mm in the thoracic spine, and 3 mm in the lumbosacral spine. Therefore, the upper limit of normal or the thresholds of instability may be smaller for the Y-axis. Accordingly, measuring techniques in the Y-axis may need to be more exacting and precise.

Embodiments of the present invention may utilize accelerometers, inclinometers and/or electronic linear displacement gauges as electronic sensors which can measure the data between each vertebral segment, each with a sensor anchored to it, and measure with regard to roll, pitch, and yaw.

In one embodiment, the device may include communication capabilities for interacting with other equipment, for example, a computer generated image recreation system. It may, for example, be incorporated for use with computer aided surgical navigation systems, such as VectorVision available from BrainLab, Inc. of Germany, OrthoPilot, available from Aesculap, Inc. of Germany, HipNav, available from Casurgica, Inc., of Pittsburgh, Pa., and Navitrack, available from Orthosoft-Centerpulse Orthopedics, of Austin, Tex. In one such embodiment, data received from a sensor may be used by the computer system. The computer or other electronic instrument may be configured to activate the appropriate controls or devices as necessary based on the data received from the sensor. Manual adjustments may also be made in response to the data received from the sensor. In another such embodiment, data from the sensor can be used in a feedback loop to maintain a desired property such as an orientation or position. Upon attachment of the device to a surgical instrument, an operator, such as a surgeon for example, can use the device to obtain three-dimensional orientation information. This combination of the device with a surgical instrument is useful for assisting surgical procedures.

Embodiments of the middle column measurement guide may include a microelectromechanical system (MEMS) comprised by tri axis (X, Y, and Z) gyroscopes or three linear gyroscopes arranged in the X, Y, and Z axis in order to measure displacement and angular velocity or motion of the middle column. The accelerometers, gyroscopes, triaxial gyroscopes and MEMS components are integrated to measure the relative motion and height restoration of the middle column. There can be one anchor above and one below the spinal segment or separate anchors in each of the intervening vertebral segments. The MEMS gyroscopes, accelerometers and/or inclinometers may be used to measure and quantitate linear displacement, angular change in motion and/or the strain between the vertebral levels from the perspective of the middle column.

The following case studies and tests are intended to illustrate various aspects of the invention, and are not intended to limit the scope of the invention.

Figure 17:
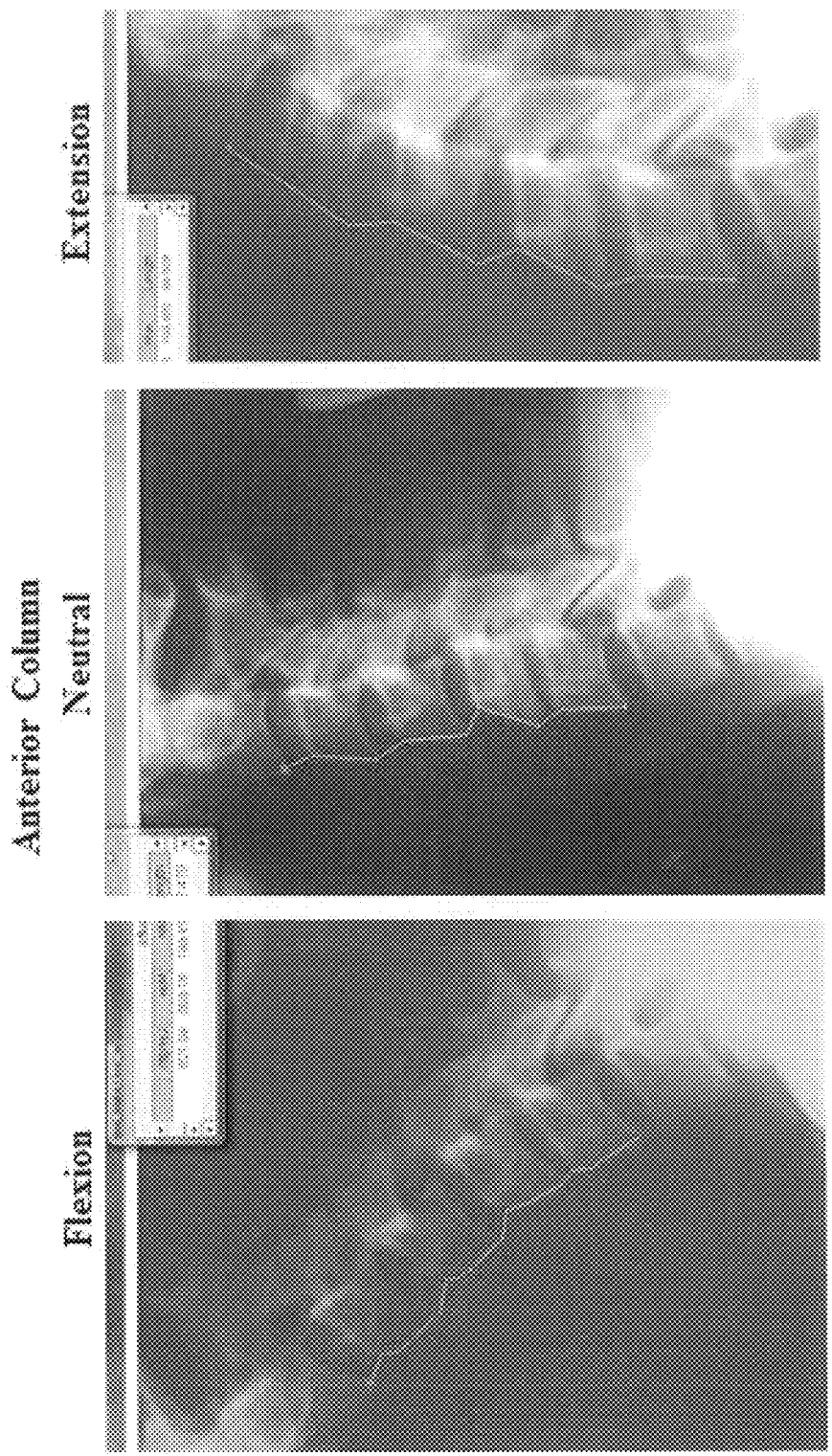
FIGS. 17-19 are spinal images.
Figure 18:
Figure 19:
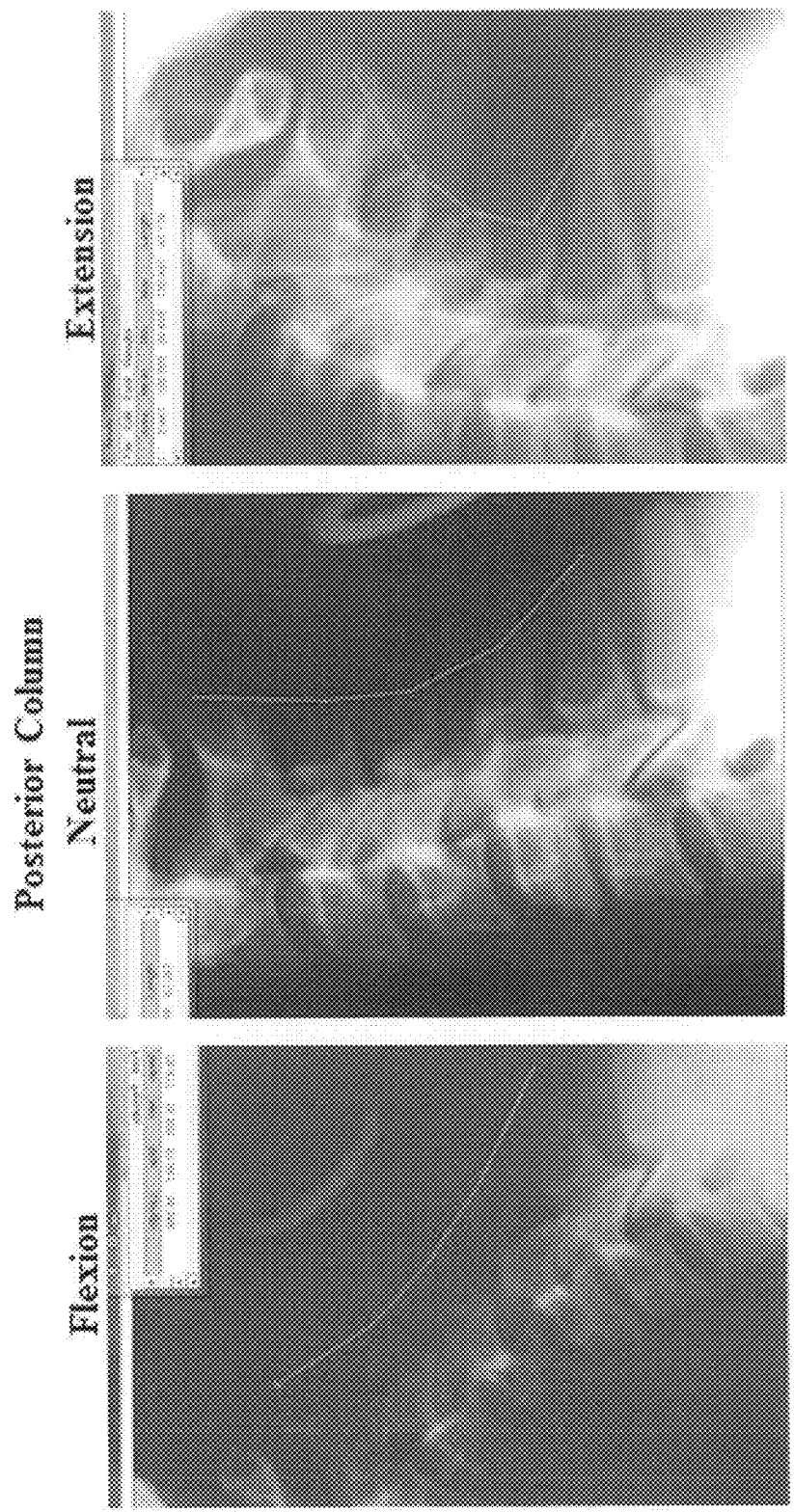

A study was done using twenty-four patients with cervical flexion and extension radiographs to determine the effect of posture on middle column gap balancing measurements. FIG. 17 shows radiographs in flexion, neutral and extension positions, with lines drawn along the anterior column for each position. FIG. 18 shows radiographs in flexion, neutral and extension positions, with lines drawn along the middle column for each position. FIG. 19 shows radiographs in flexion, neutral and extension positions, with lines drawn along the posterior column for each position. Measurements along the middle column were more accurate and least influenced by measurements of spinal height on the front (anterior column) and back (posterior column).

Figure 20:
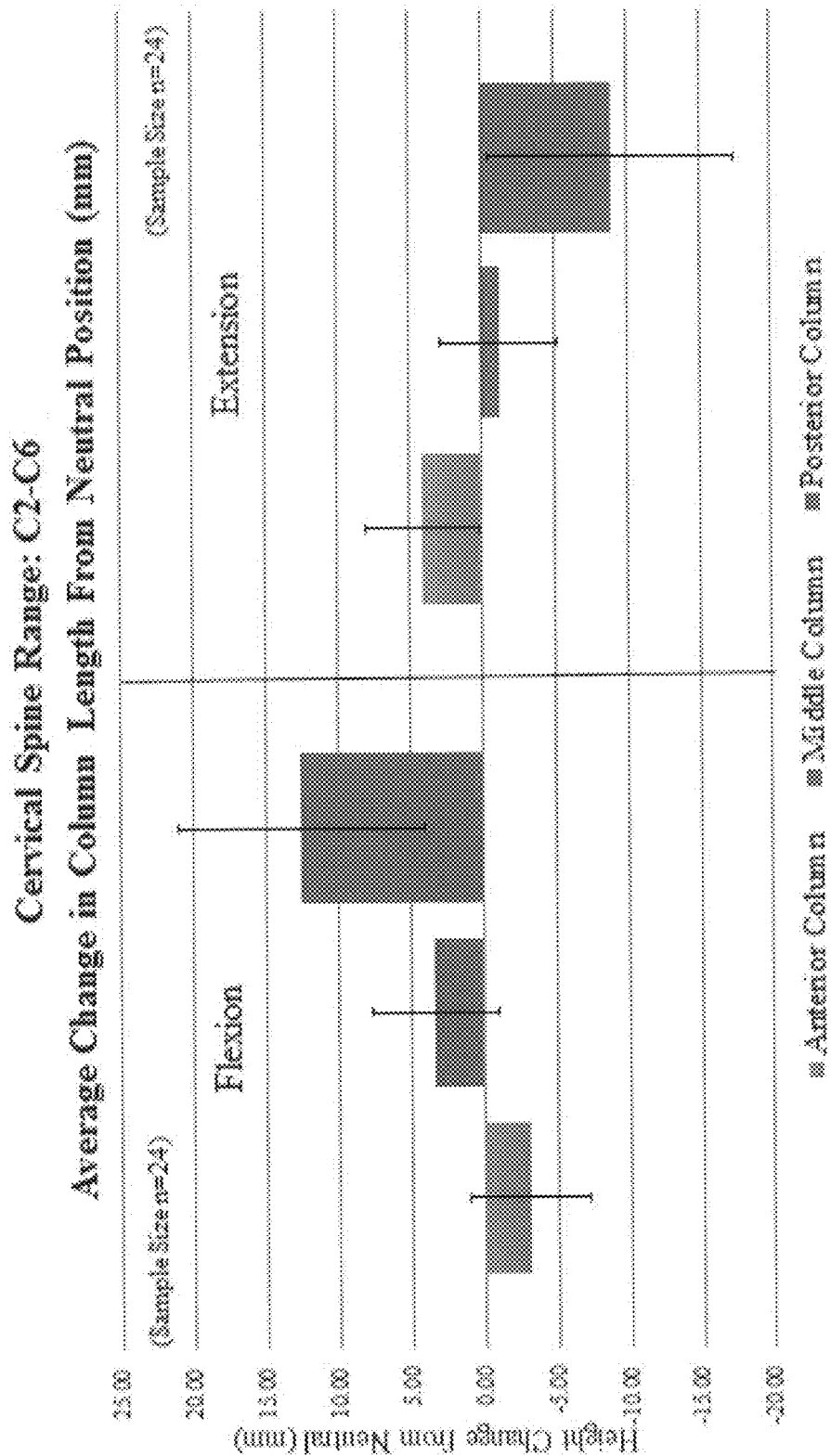
FIGS. 20 and 21 are graphs illustrating differences between measurements made at the anterior column, middle column and posterior column during flexion and extension.
Figure 21:
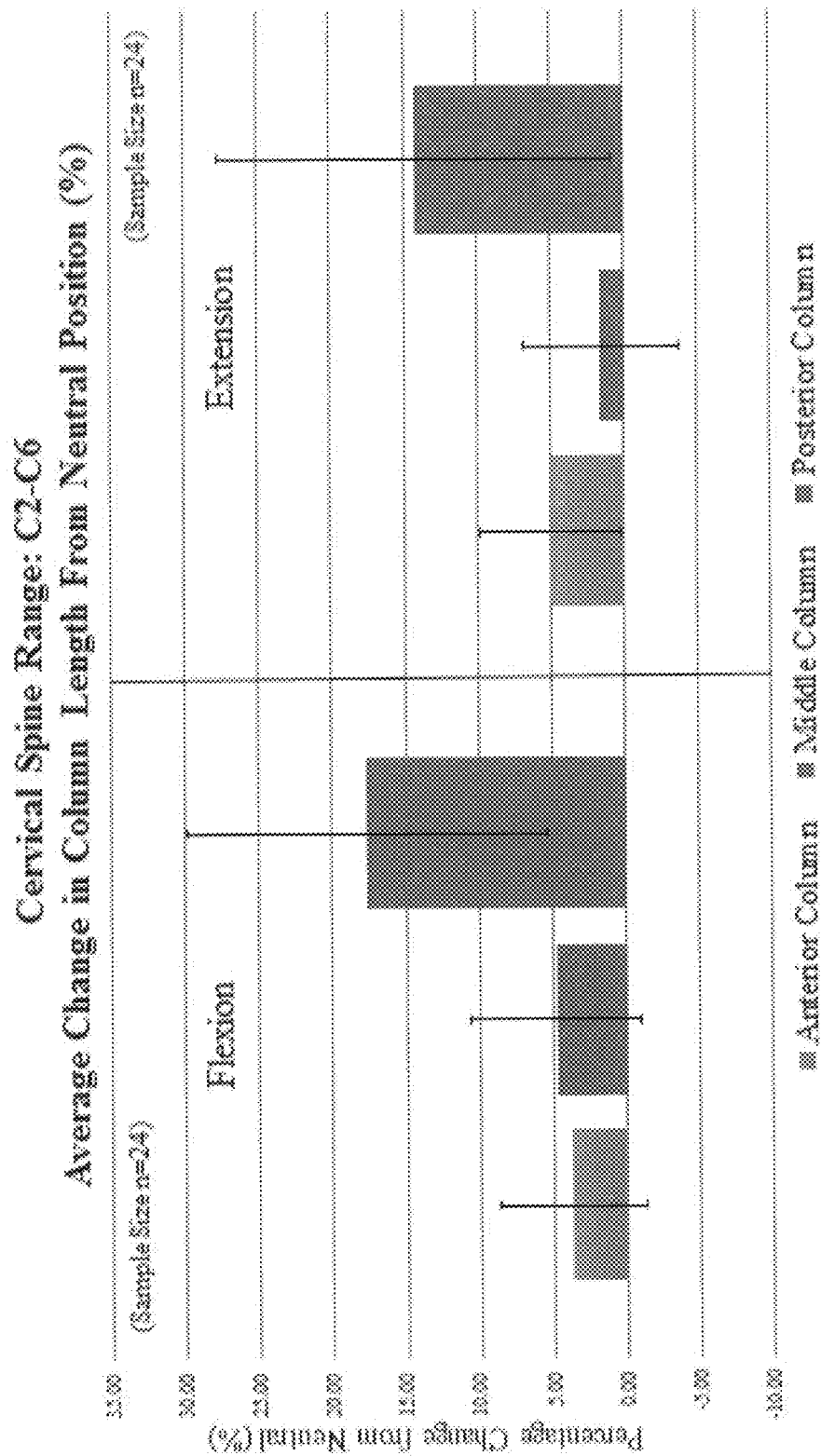

The comparative changes in anterior, middle and posterior column length under flexion and extension are referenced to neutral. These are represented as values (+/− mm) and percent (%) change from the neutral conditions. FIG. 20 graphically illustrates the height change in column length in flexion and extension from neutral when measured at the anterior column, middle column and posterior column. FIG. 21 graphically illustrates the percentage change in column length in flexion and extension from neutral when measured at the anterior column, middle column and posterior column. In flexion, the anterior column length decreases and middle and posterior columns increase because they are behind the center of rotation. In extension, the opposite occurs, posterior and middle column length decrease and anterior column length increases. The present middle column measurement techniques are accurate throughout all postures because the middle column corresponds to the center of rotation of the spine.

Figure 22:
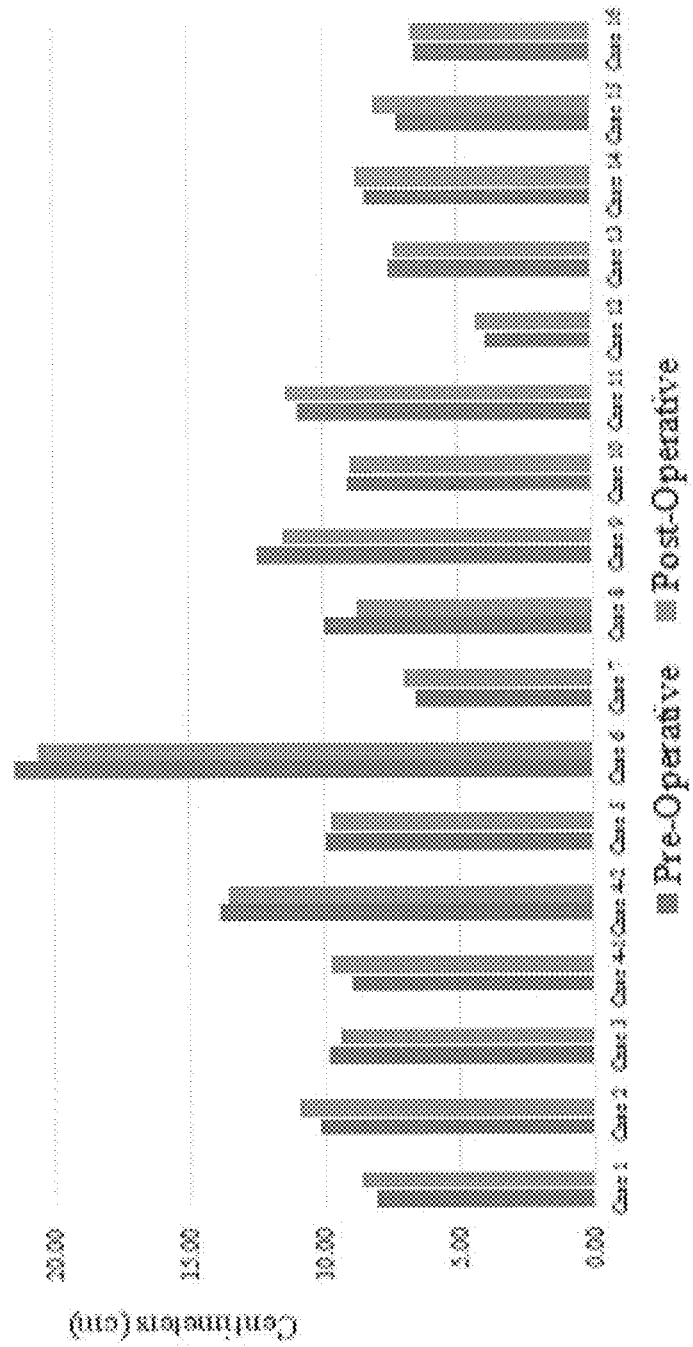
FIGS. 22 and 23 are graphs illustrating middle column gap balancing measurements made in accordance with embodiments of the present invention.
Figure 23:
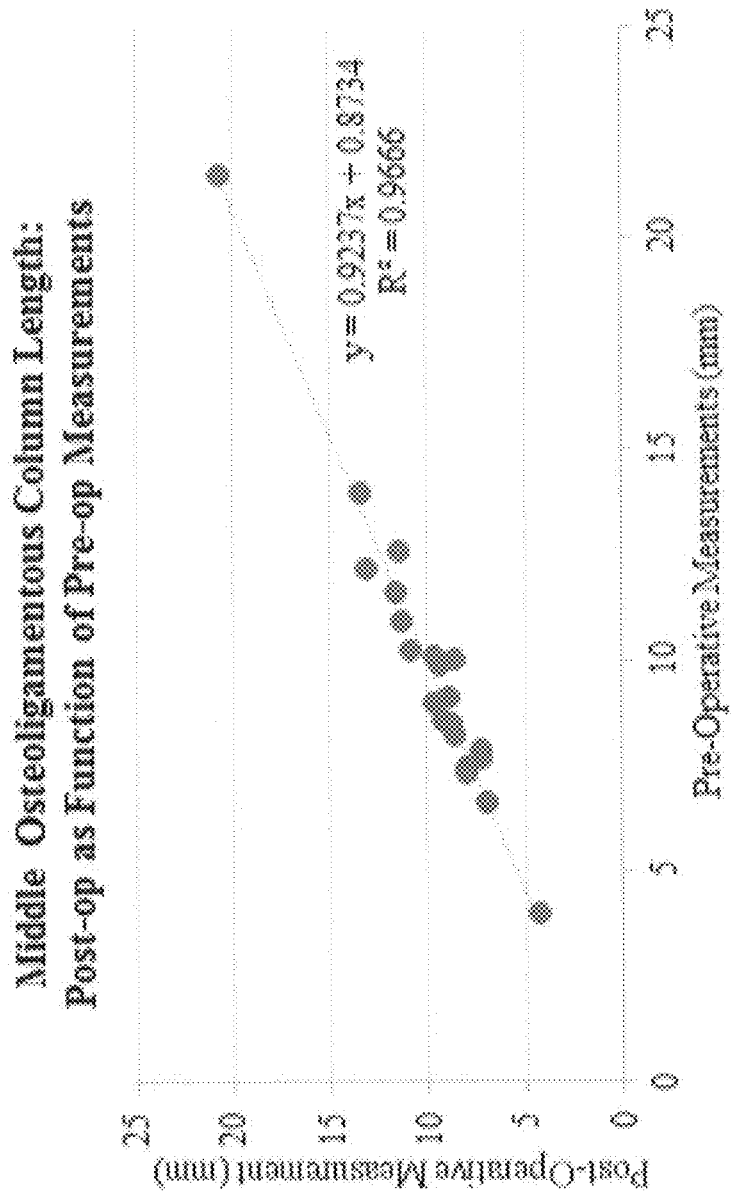

Middle column gap balancing measurements were made on patients in accordance with methods of the present invention. Pre-operative and post-operative measurements are listed in Table 1 and graphically shown in FIGS. 22 and 23.

TABLE 1

MCGB Measurements
Middle Osteoligamentous Column Measurements

| Case Number | Measurements (cm) | |
| --- | --- | --- |
| | Pre-Operative | Post-Operative |
| Case 1 | 8.17 | 8.67 |
| Case 2 | 10.15 | 10.97 |
| Case 3 | 9.82 | 9.42 |
| Case 4-1 | 8.94 | 9.70 |
| Case 4-2 | 13.89 | 13.58 |
| Case 5 | 10.01 | 9.79 |
| Case 6 | 21.44 | 20.67 |
| Case 7 | 6.55 | 7.08 |
| Case 8 | 9.94 | 8.75 |
| Case 9 | 12.50 | 11.50 |
| Case 10 | 9.10 | 8.95 |
| Case 11 | 10.90 | 11.35 |
| Case 12 | 3.97 | 4.28 |
| Case 13 | 7.61 | 7.35 |
| Case 14 | 8.45 | 8.81 |
| Case 15 | 7.28 | 8.08 |
| Case 16 | 12.11 | 13.20 |
| Case 17 | 7.4 | 8.18 |
| Case 18 | 8.51 | 9.29 |
| Case 19 | 7.8 | 7.37 |
| Case 20 | 11.53 | 11.69 |

A paired t-test was run on a sample of twenty-one patients to determine whether there was statistical significance between pre-operative and post-operative measurements of the middle osteoligamentous column. Increases in middle column length following surgery were negligible (post-op: 9.9±3.7 cm; pre-op: 9.8±3.4 cm). No statistical difference was found between column lengths (95% CI, −0.42 to 0.17) cm,t(20)=−0.871, p<0.394, d=20.

A Pearson product-moment correlation was run to determine the relationship between each individual's pre-op and post-op middle osteoligamentous column measurements. There was a strong, positive correlation between pre-operative and post-operative measurements, which was statistically significant (r=0.983, n=21, p<0.01). This shows that the present method is highly predictive of optimal post-operative spinal height.

Figure 24:
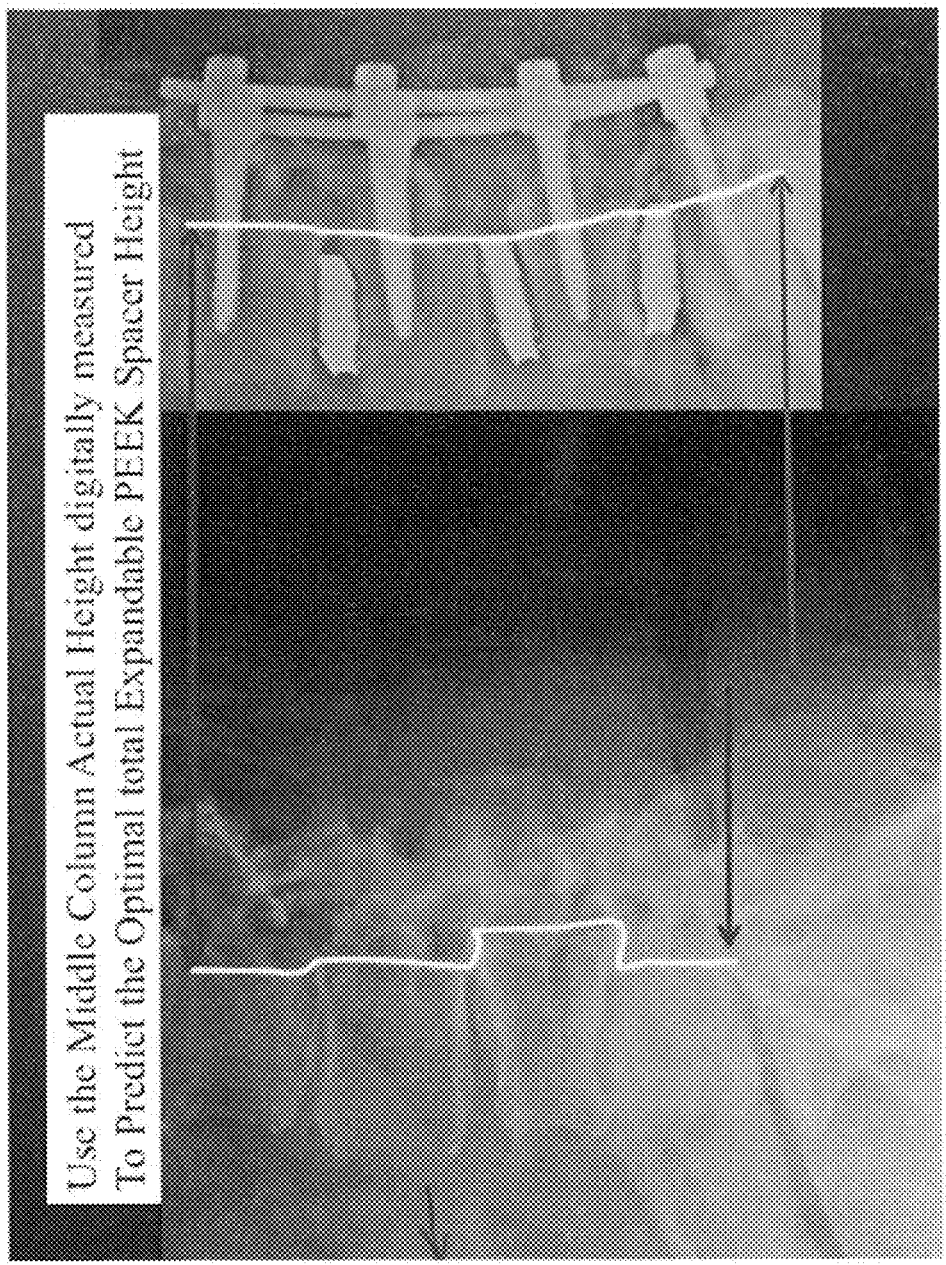
FIGS. 24-39 are spinal images illustrating middle column measurement methods in accordance with various embodiments of the present invention.

FIG. 24 shows a lumbar spine case. The pre-operative lumbar spine from sagittal or lateral digital radiographic image is on the left, and the post-operative image is on the right in the radiographs.

Figure 25:
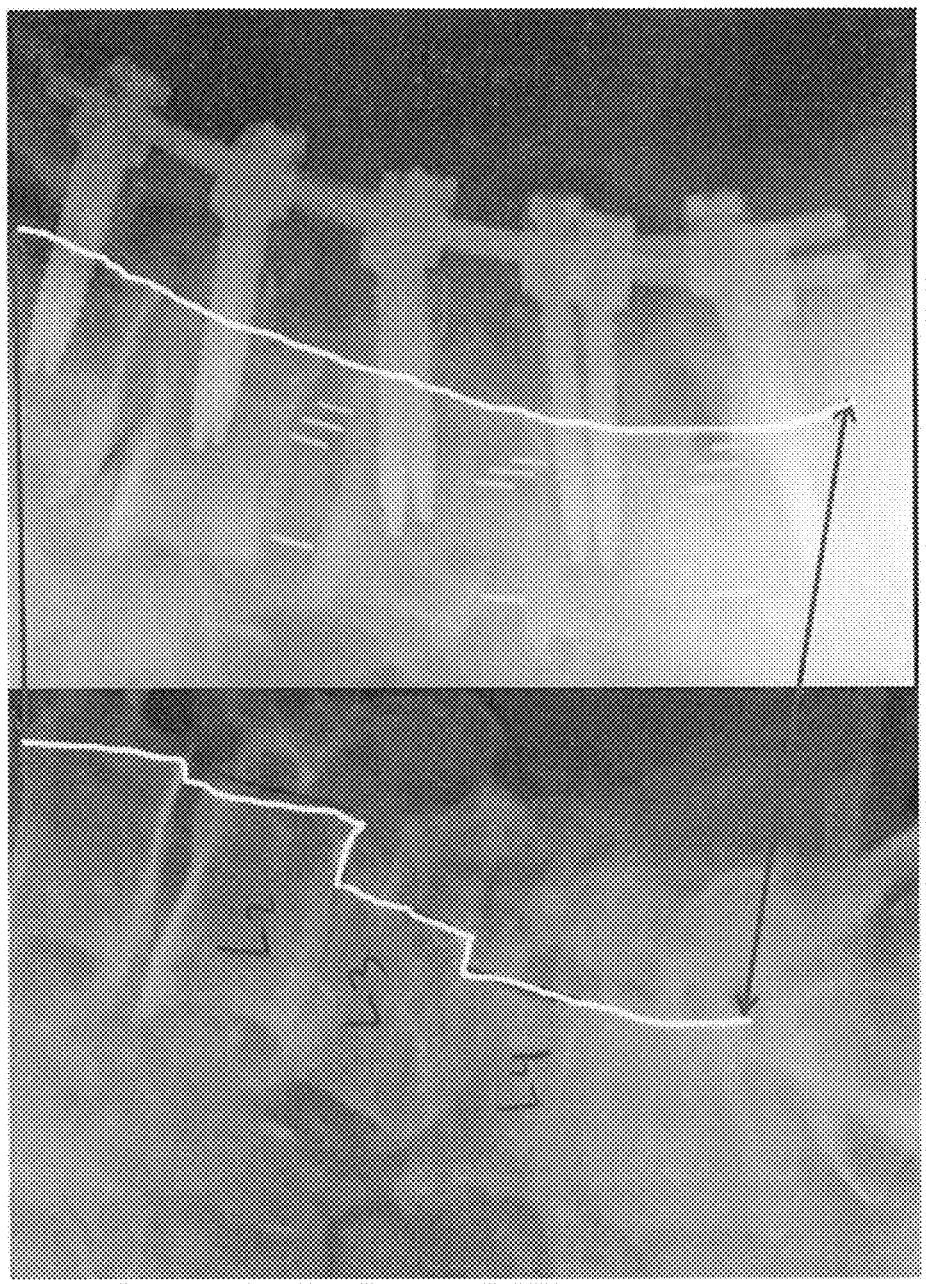

FIG. 25 shows another lumbar spine case. The pre-operative image is on the left, and the postoperative image is on the right.

Figure 26:
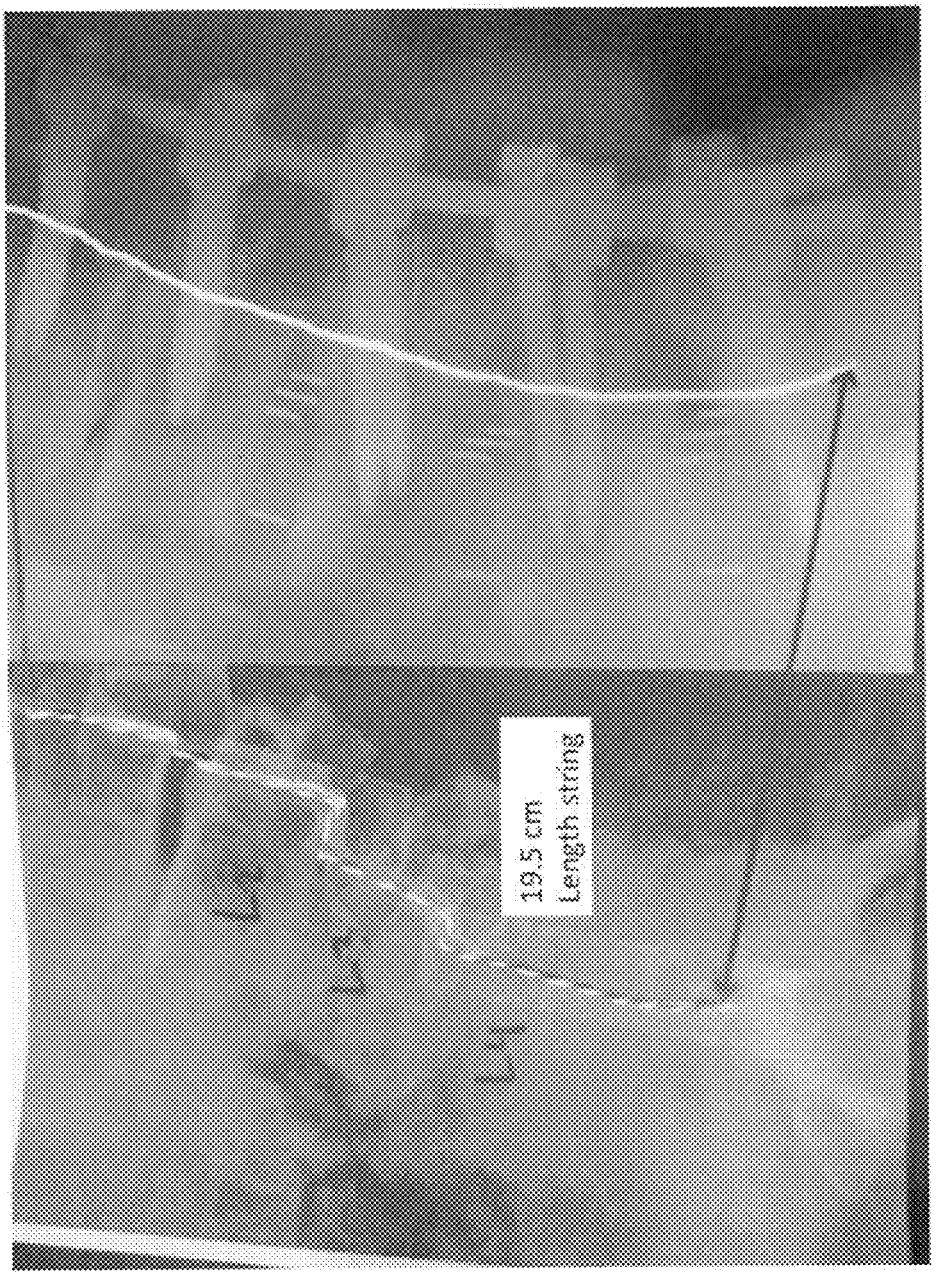
Figure 27:
Figure 28:

FIGS. 26-28 show another lumbar spine case. In FIG. 26, the dashed line is 19.5 cm long. FIG. 27 shows that the apparent MC height is 16 cm when measured as the shortest distance from the posterior corners of L1 and L5 vertebral bodies. The length of the dashed line is 3.5 cm longer than the apparent L1 to L5 preoperative shortest perpendicular distance. Thus, there is a mismatch of middle column or PLL height of 19.5 minus 16 cm=3.5 cm. From the 3.5 cm mismatch it would be expected that the surgeon could reconstruct the three intervertebral disk spaces with three 11 mm intervertebral spacers (3×11 mm-3.3 cm) which is less than 3.5 cm, so there is a safety factor to avoid neurologic compromise. FIG. 28 demonstrates that the reconstructed middle column spinal length at the PLL is the appropriate length of 19.5 cm.

Figure 29:
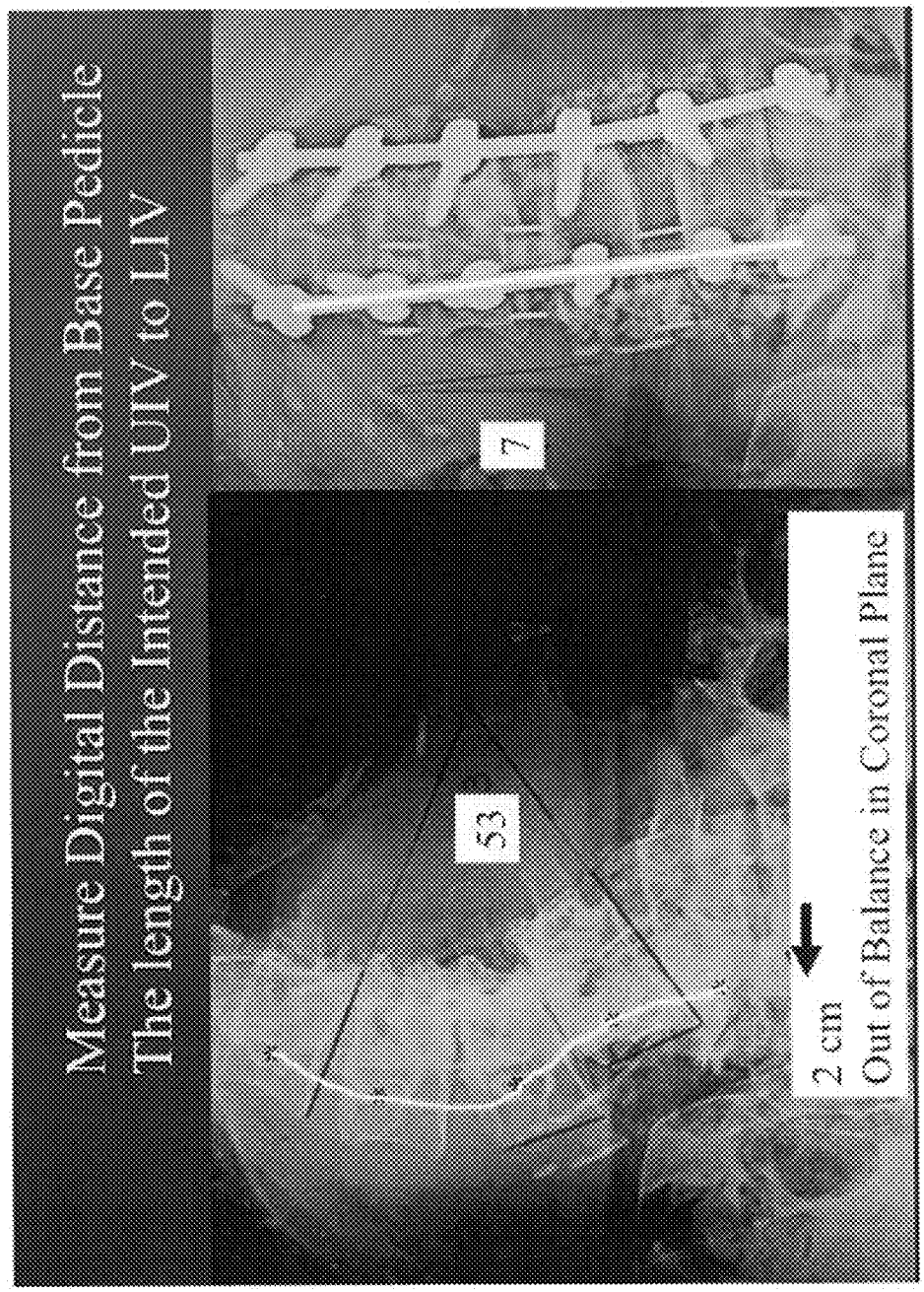

A three dimensional case is shown in FIG. 29. In addition to the sagittal plane deformity, the coronal plane can also be addressed by measuring the middle column along the convex side of the base of the pedicles which are in an approximate anatomic location to the middle column. The convex side of a coronal spinal deformity is digitally measured using a line from vertebral endplate to endplate intersecting the ipsilateral pedicles on the convex side (from top to bottom, from superior to inferior, from cranial to cephalad). UIV is upper instrumented vertebra and LIV is lower instrumented vertebra. This anteroposterior measurement on the coronal plane can be made from pedicle-to-pedicle, or it can be made from the L1 upper vertebral endplate to the lower vertebral endplate of L5.

Figure 30:
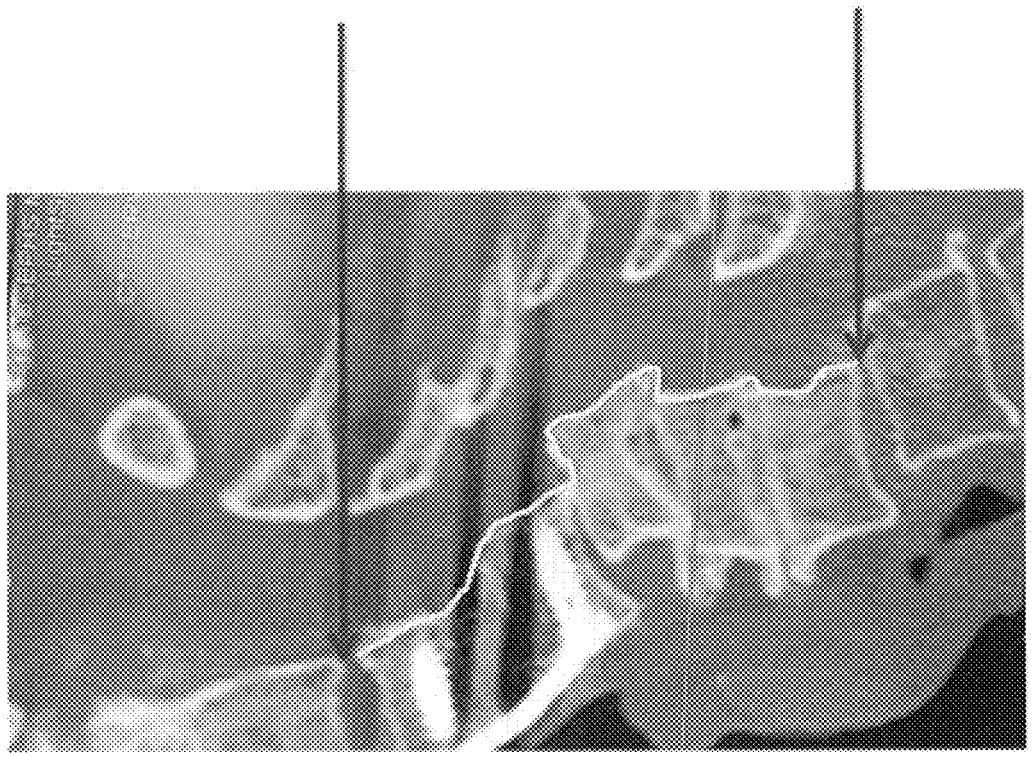
Figure 31:
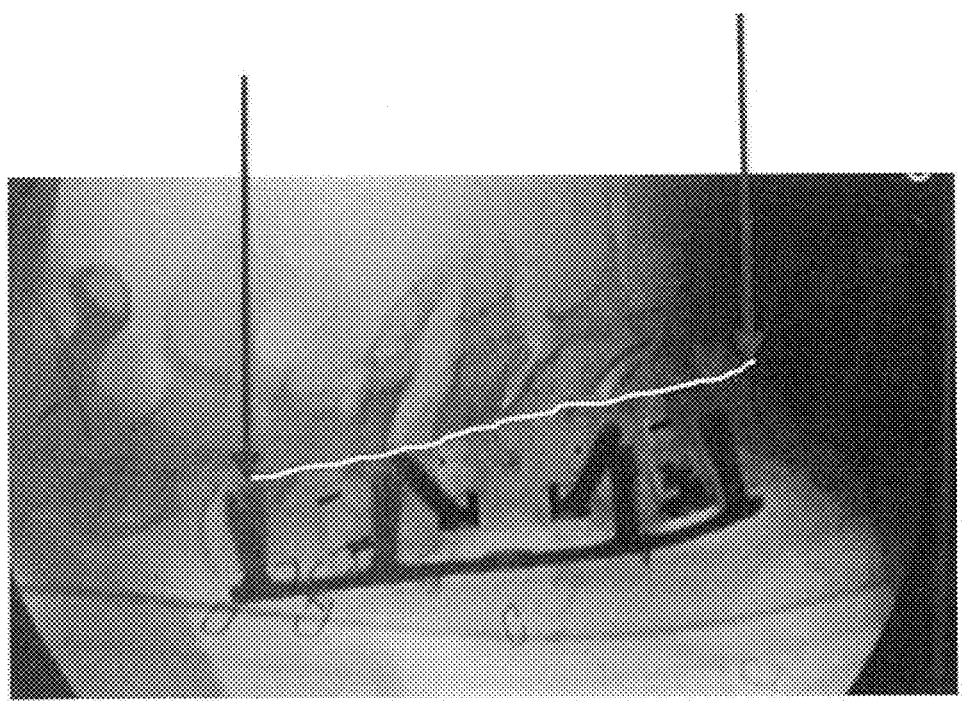

FIGS. 30 and 31 show pre-operative and post-operative images for a patient who had sustained C4-5 subluxation, perched facet, C5 retrodisplacement, and C3 to C7; with cervical kyphosis, 4 cm of C2-C7 SVA translation. In pre-operative FIG. 30, the highlighted line is the digitally measured height of the middle osteoligamentous column from the posterior-inferior corner of C2 to the posterior-inferior corner of C7. In post-operative FIG. 31, the highlighted line is the digitally measured restored middle column height from the posterior-inferior corner of C2 end plate to the posterior-inferior corner of C7 end plate.

Figure 32:
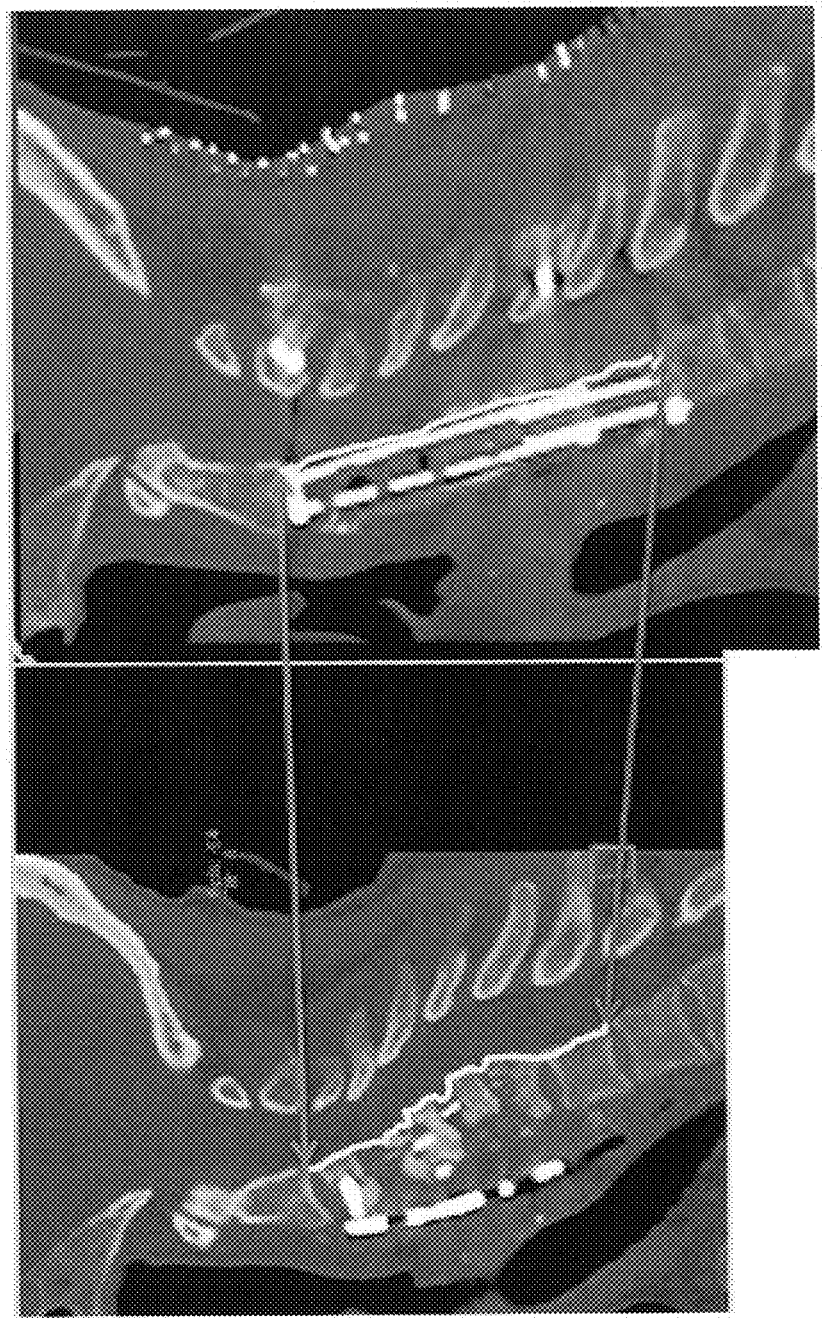

FIG. 32 shows a case involving rheumatoid arthritis with basilar invagination. The length of the highlighted line is measured pre-operatively and post-operatively with a goal of decreasing the mismatch between the two. Height of the middle column as the crow flies may be compared to the actual contour of the PLL (pre and post op).

Figure 33:
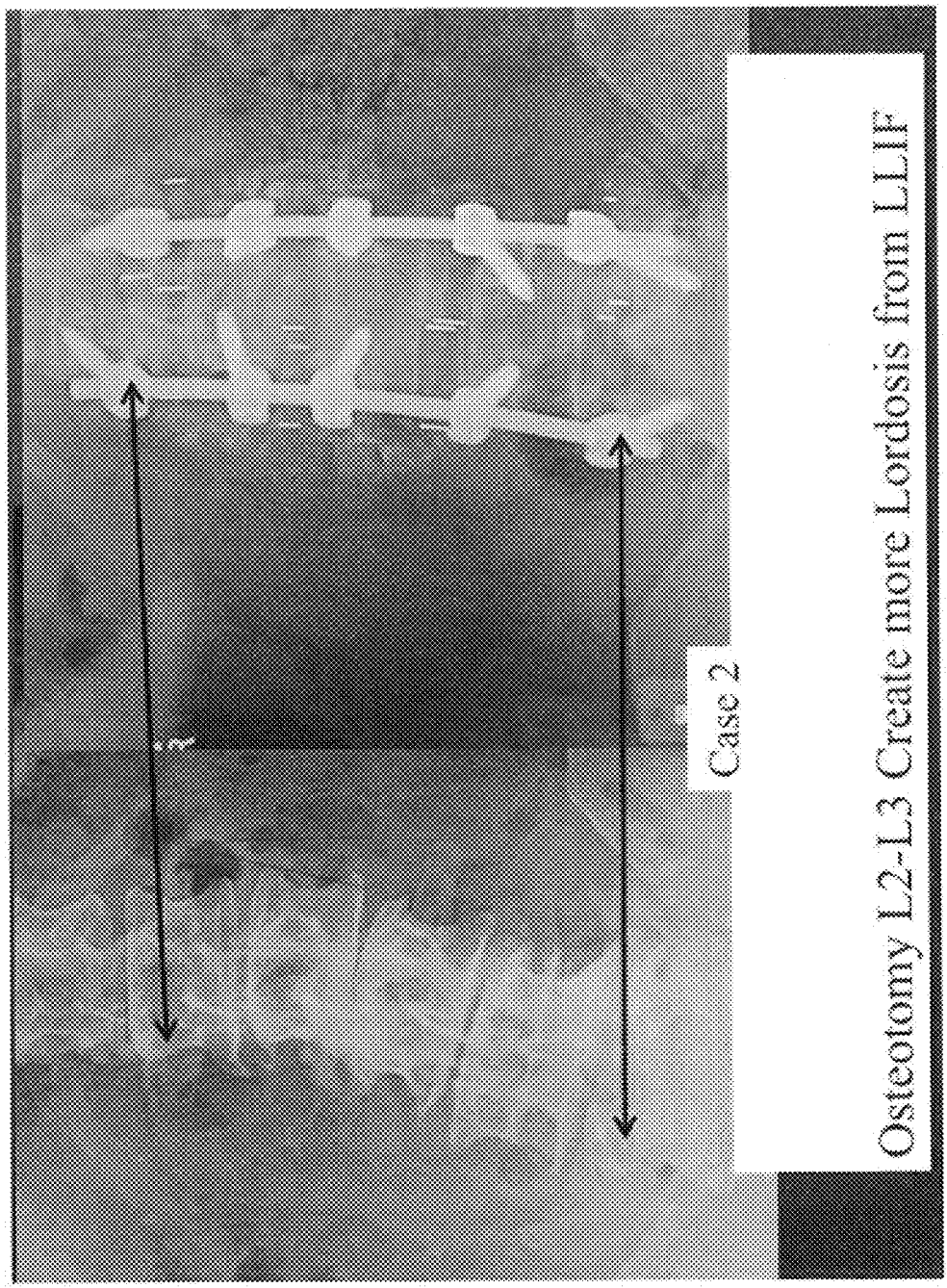
Figure 34:
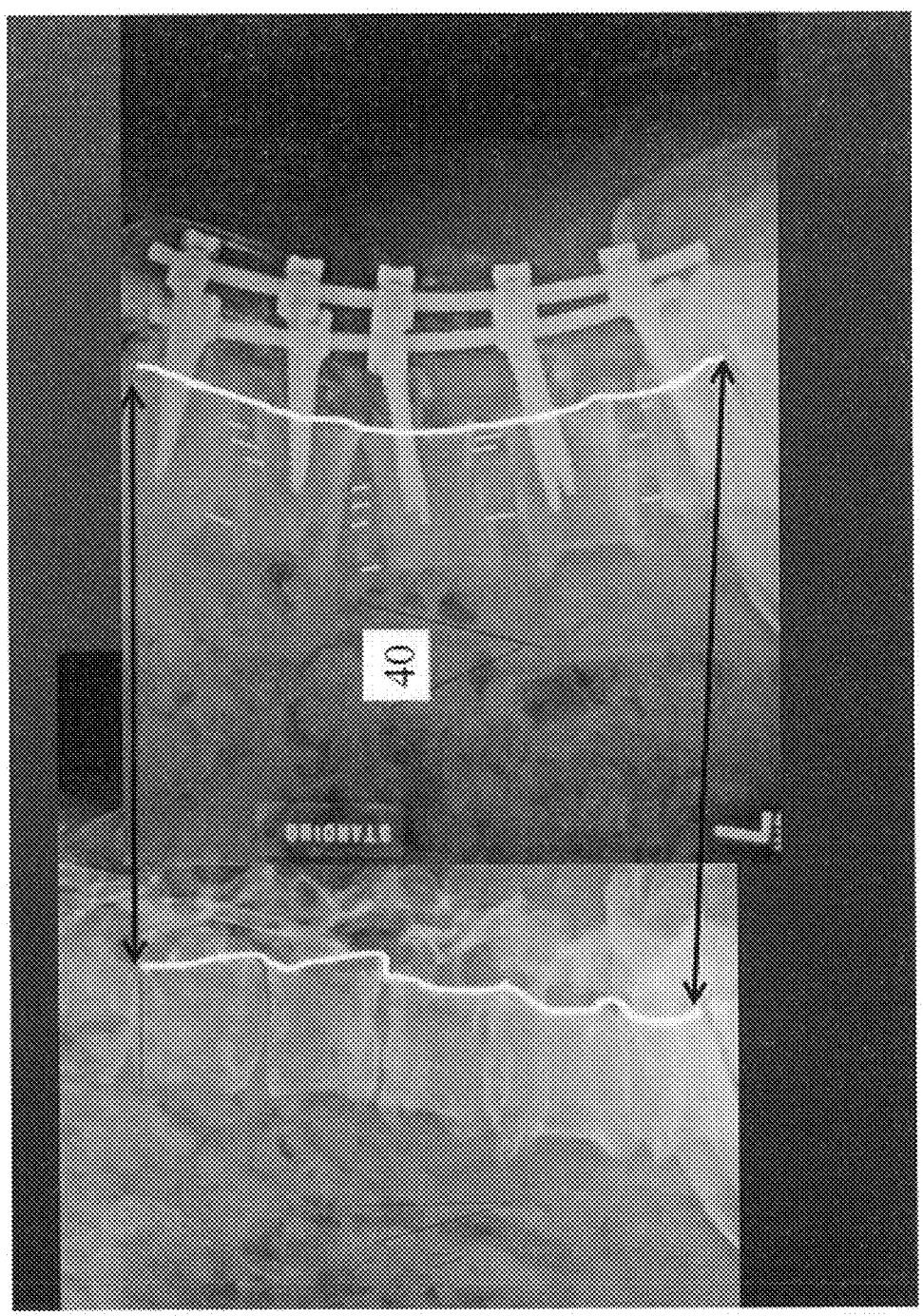

FIGS. 33 and 34 show a case involving degenerative scoliosis with spinal stenosis and neurogenic claudication. Pre-operative and post-operative images are shown in these figures. In FIG. 34, the highlighted pre-operative and post-operative middle column lines are shown. This case demonstrates that middle column measurement can be used to prevent overdistraction.

Figure 35:
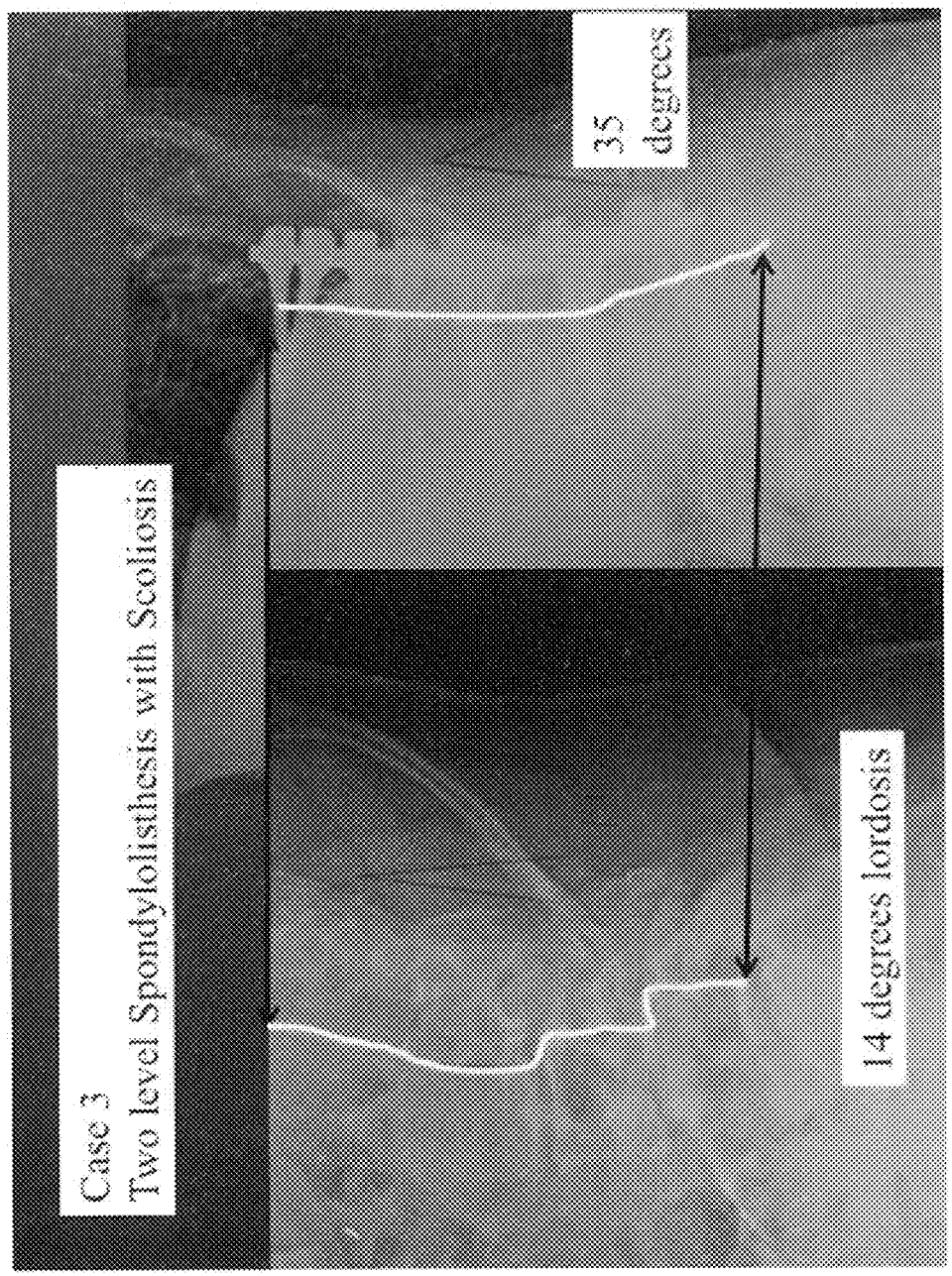

FIG. 35 shows a case involving two level spondylolisthesis with scoliosis. Highlighted pre-operative and post-operative middle column lines are shown.

Figure 36:
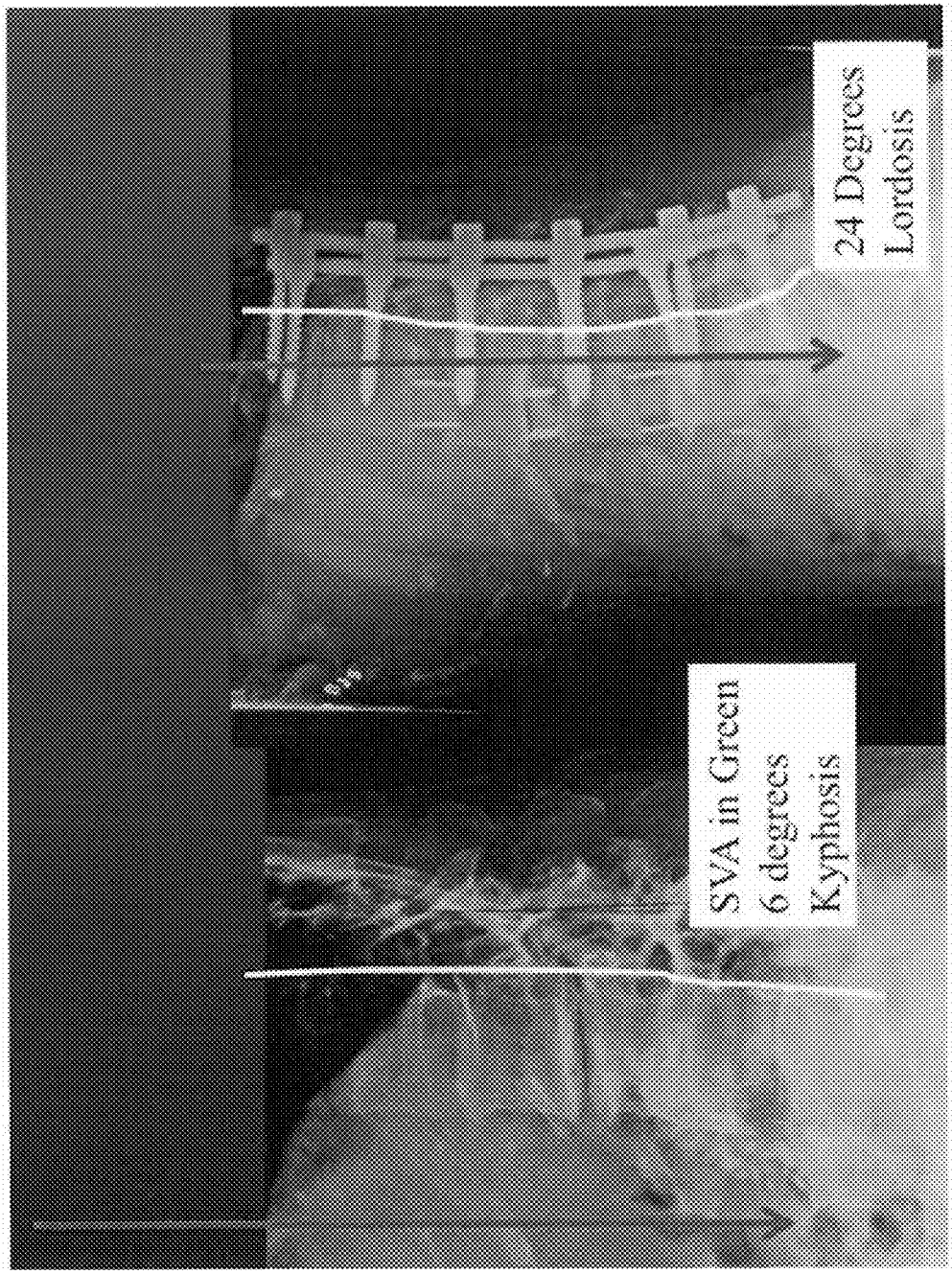

FIG. 36 shows a case of sagittal vertebral alignment (SVA). Highlighted pre-operative and post-operative middle column lines are shown.

Figure 37:
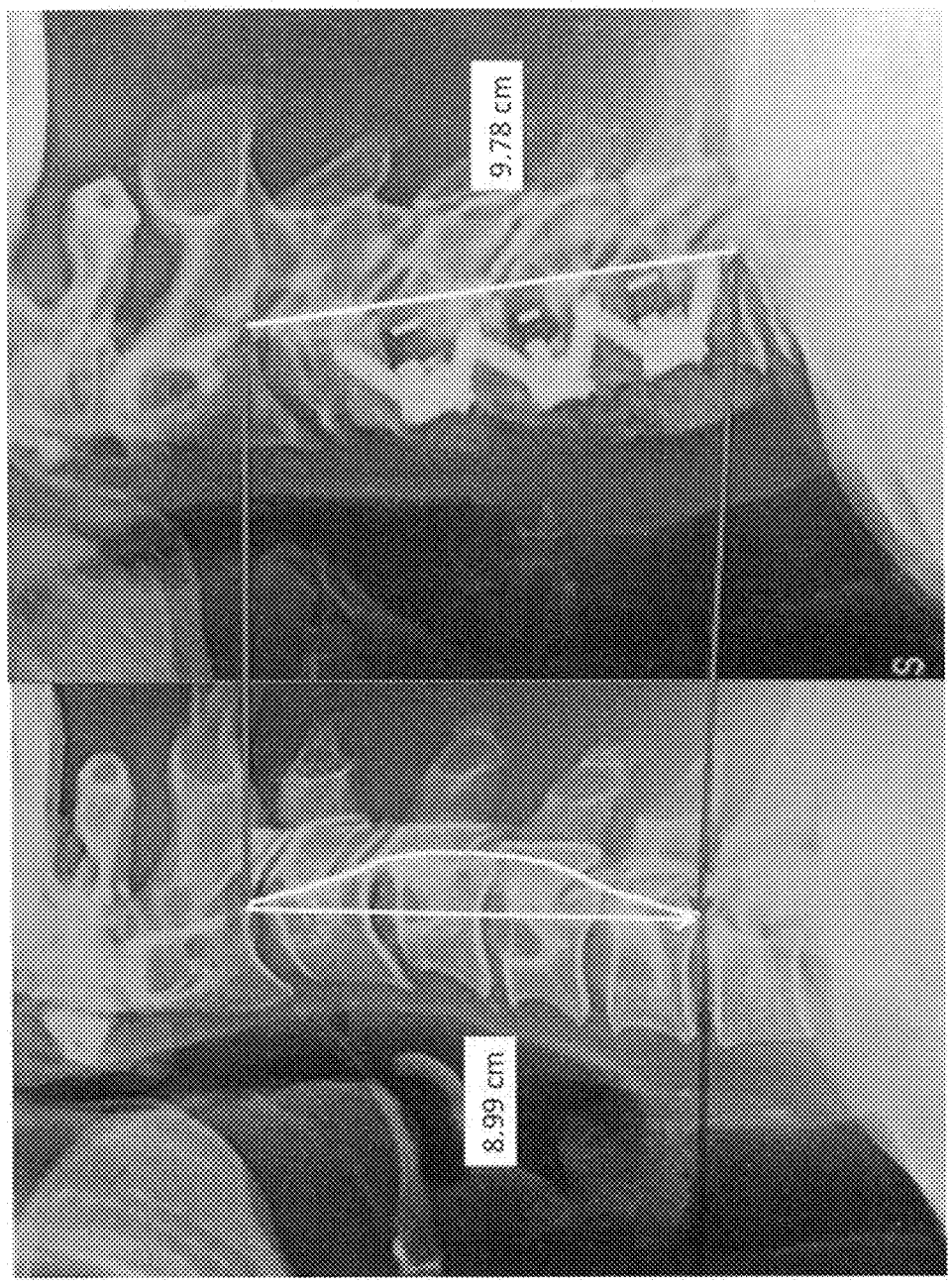

FIG. 37 shows a cervical case with three spacers inserted, which increased the MC-pedicle base height to 9.78 cm. Highlighted pre-operative and post-operative middle column lines are shown.

Figure 38:
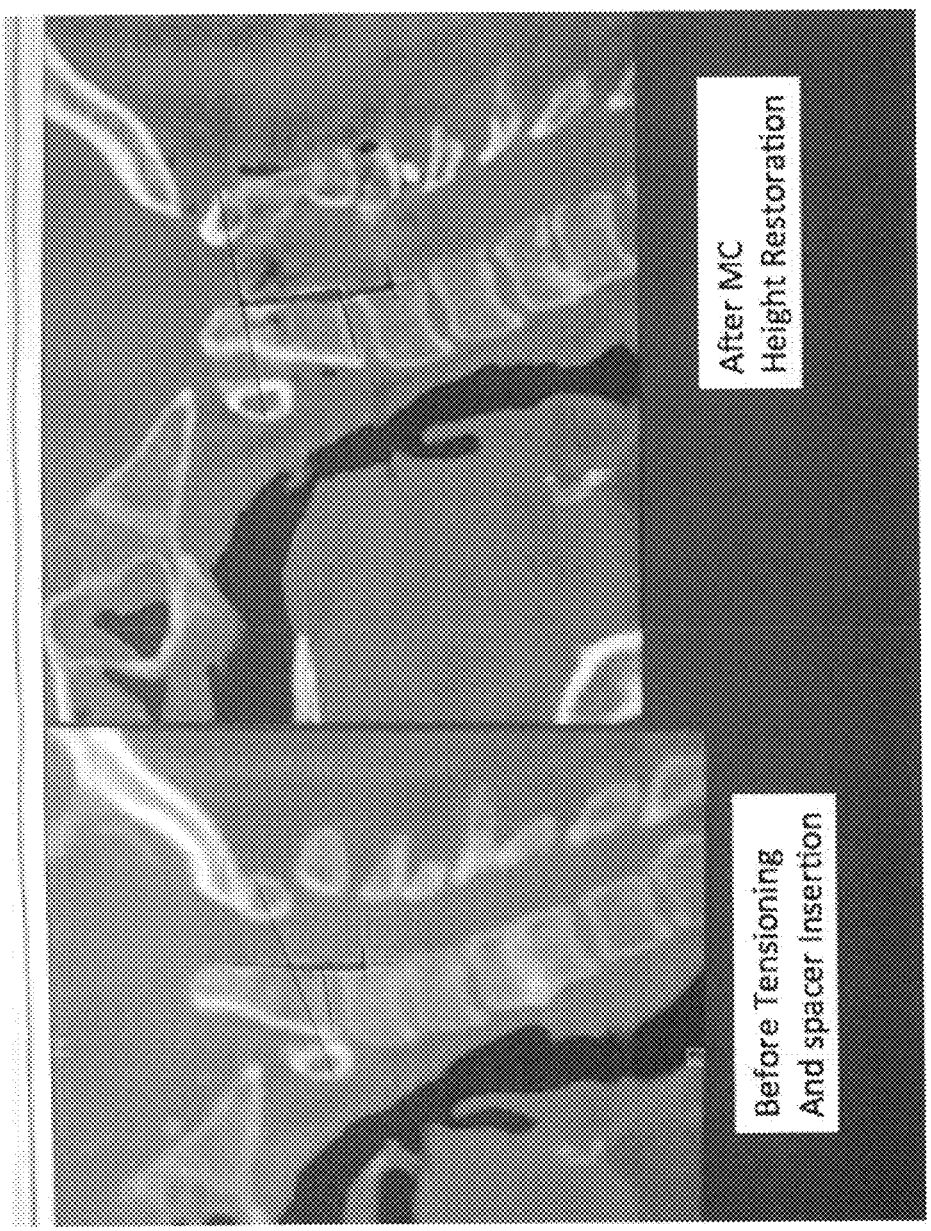

FIG. 38 shows a case of occiput to cervical spine measurement at the middle column. A line is drawn from the center of C2 pedicle to a line connecting the anterior and posterior C1 arches. A normal measurement in men is 17 mm, whereas in women it is 15 mm. A distance of <13 mm is consistent with impaction. Less than 7 mm is associated with medullary compression on MR image. Therefore, 16 mm−13 mm=3 mm is a lower limit of normal axial instability along middle column to the line connecting the anterior and posterior C1 arches.

Figure 39:
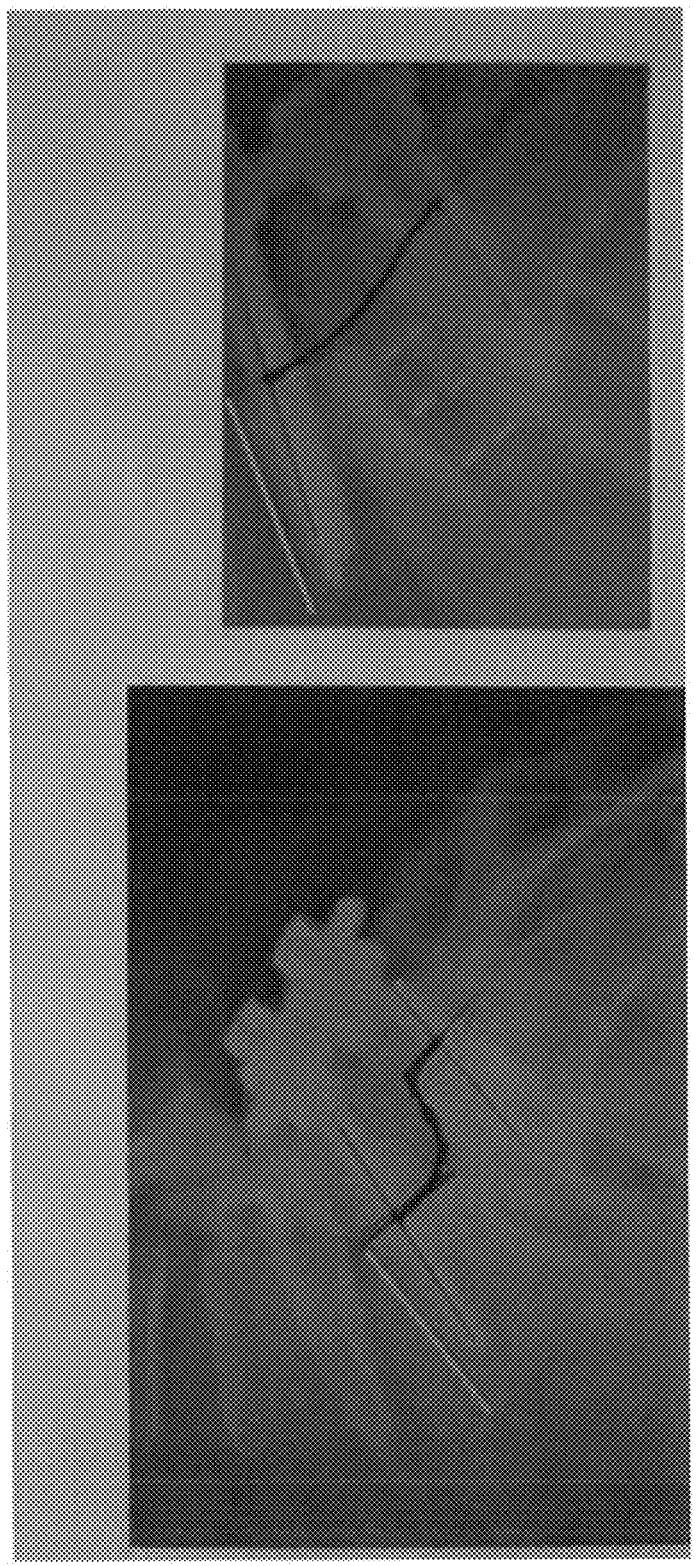

FIG. 39 shows measurement of middle column height at the extreme lower end of the spine, L5 to S1 with L5-S1 spondylolisthesis.

Embodiments of the present invention provide measurement of structures in the spine, which has predictive value to improved neurologic and/or clinical functional outcomes. Predictive value for optimal final height restoration of the middle osteoligamentous column (MC) and/or posterior longitudinal ligament (PLL) is provided.

Whereas particular embodiments of this invention have been described above for purposes of illustration, it will be evident to those skilled in the art that numerous variations of the details of the present invention may be made without departing from the invention as defined in the appended claims.

What is claimed is:

1. A method of measuring intervertebral spacing length at a middle column of a spine comprising:
    positioning a first middle column marker in a first vertebra, wherein the first middle column marker is located at a depth of the middle column of the first vertebra;
    positioning a second middle column marker in a second vertebra, wherein the second middle column marker is located at a depth of the middle column of the second vertebra; and
    measuring, at the middle column, a distance between the first and second middle column markers to thereby determine the intervertebral spacing length at the middle column,
    wherein the measuring comprises:
        determining a first line, within a medical image of the spine, along the middle column of the first vertebra at a point at which the first middle column marker passes through the middle column of the first vertebra;
        identifying a first point on an edge of the first vertebra where the first line intersects with the edge of the first vertebra;
        determining a second line, within a medical image of the spine, along the middle column of the second vertebra at a point at which the second middle column marker passes through the middle column of the second vertebra;
        identifying a second point on an edge of the second vertebra where the second line intersects with the edge of the second vertebra; and
        measuring a distance between the first point and the second point
        wherein the distance between the first point and the second point represents the distance between the first and second middle column markers; and
    wherein the middle column comprises a region on the spine, wherein the region is bounded on a first side by a posterior surface of a vertebral body of a vertebra, and wherein the region is bounded on a second side located at a distance between substantially one-third and substantially one-half through the vertebral body from the posterior surface to an anterior surface of the vertebral body.

2. The method of claim 1, wherein the first middle column marker is provided on a first bone anchor, and the second middle column marker is provided on a second bone anchor.

3. The method of claim 2, wherein each of the first and second bone anchors comprises a pedicle screw or pin.

4. The method of claim 3, wherein the first and second middle column markers comprise a detectable feature on the pedicle screw or pin.

5. The method of claim 4, wherein the detectable feature comprises a shoulder on a shaft of the pedicle screw or pin.

6. The method of claim 2, further comprising:
attaching a distraction tool to the first and second bone anchors;
distracting the first and second bone anchors away from each other with the distraction tool; and
measuring a distracted intervertebral spacing length at the middle column corresponding to a distracted distance between the first and second middle column markers.

7. The method of claim 6, further comprising measuring distraction force applied by the distraction tool against the first and second bone anchors.

8. A method of measuring spinal length at a middle column of a spine comprising:
tracing a posterior longitudinal ligament on a medical image of the spine, wherein the posterior longitudinal ligament is located within the middle column;
identifying, on the traced posterior longitudinal ligament, a location of the middle column for individual vertebra along at least a portion of a length of the spine;
performing, on the traced posterior longitudinal ligament, a measurement of the length of each of the vertebrae, the measurement occurring at the middle column;
measuring, on the traced posterior longitudinal ligament, intervertebral lateral offset distances between adjacent vertebrae; and
determining an overall spinal length representing a combination of the measured lengths of the vertebrae at the middle column and the measured intervertebral lateral offset distances,
wherein the middle column comprises a region on the spine, wherein the region is bounded on a first side by a posterior surface of a vertebral body of a vertebra, and wherein the region is bounded on a second side located at a distance between substantially one-third and substantially one-half through the vertebral body from the posterior surface to an anterior surface of the vertebral body.

9. A method of measuring intervertebral tension of a posterior longitudinal ligament of a spine comprising:
positioning a first bone anchor in a first vertebra within a middle column of the spine;
positioning a second bone anchor in a second vertebra within the middle column of the spine;
distracting the first and second vertebrae by applying force against the first and second bone anchors; and
measuring tension of a posterior longitudinal ligament between the first and second vertebrae at different distraction distances,
wherein the middle column comprises a region on the spine, wherein the region is bounded on a first side by a posterior surface of a vertebral body of a vertebra, and wherein the region is bounded on a second side located at a distance between substantially one-third and substantially one-half through the vertebral body from the posterior surface to an anterior surface of the vertebral body.

10. The method of claim 9, further comprising establishing an intervertebral spacer length based upon the measured tension.

11. A method of spinal reconstructive surgery comprising:
measuring a pre-operative spinal length at a middle column of the spine, the measuring comprising:
tracing a posterior longitudinal ligament on a medical image of the spine, wherein the posterior longitudinal ligament is located within the middle column;
identifying, on the traced posterior longitudinal ligament, a location of the middle column for individual vertebra along at least a portion of a length of the spine;
performing, on the traced posterior longitudinal ligament, a measurement of the length of each of the vertebrae, the measurement occurring at the middle column;
measuring, on the traced posterior longitudinal ligament, intervertebral lateral offset distances between adjacent vertebrae; and
determining an overall spinal length representing a combination of the measured lengths of the vertebrae at the middle column and the measured intervertebral lateral offset distances; and
establishing at least one intervertebral spacing in the spine based on the measured pre-operative spinal length at the middle column,
wherein the middle column comprises a region on the spine, wherein the region is bounded on a first side by a posterior surface of a vertebral body of a vertebra, and wherein the region is bounded on a second side located at a distance between substantially one-third and substantially one-half through the vertebral body from the posterior surface to an anterior surface of the vertebral body.

12. A method for measuring rotational displacement of adjacent vertebrae of a spine comprising:
positioning a middle column marker in at least two vertebrae of the spine within a middle column of the spine;
applying a force between the middle column markers; and
measuring relative angular movement between the middle column markers,
wherein the middle column comprises a region on the spine, wherein the region is bounded on a first side by a posterior surface of a vertebral body of a vertebra, and wherein the region is bounded on a second side located at a distance between substantially one-third and substantially one-half through the vertebral body from the posterior surface to an anterior surface of the vertebral body.

13. The method of claim 12, where the force is applied by a distraction tool.

14. An apparatus for measuring intervertebral spacing distances between adjacent vertebrae at a middle column of a spine comprising:
a first middle column marker, wherein the first middle column marker is positionable in the spine at a depth of a middle column of a first vertebra;
a second middle column marker, wherein the second middle column marker is postitionable in the spine at a depth of a middle column of a second vertebra; and
a detector capable of measuring a distance between the first and second middle column markers at the middle column to thereby determine the intervertebral spacing length at the middle column, wherein the middle column comprises a region on the spine, wherein the region is bounded on a first side by a posterior surface of a vertebral body of a vertebra, and wherein the region is bounded on a second side located at a distance between substantially one-third and substantially one-half through the vertebral body from the posterior surface to an anterior surface of the vertebral body.

15. An intervertebral tension measuring apparatus for measuring intervertebral tension and identifying intervertebral spacer lengths comprising:

a distractor engageable with bone anchors installed in adjacent vertebrae within a middle column of a spine;

a tension measurement device structured and arranged to measure amounts of force applied by the distractor against the bone anchors when the vertebrae are separated from each other by the distractor against tension applied by a posterior longitudinal ligament of the spine; and a distance correlating device structured and arranged to record varying distances between the adjacent vertebrae in the middle column and correlating each of the varying distances with a force measured by the tension measuring device corresponding to the tension applied by the posterior longitudinal ligament, wherein the middle column comprises a region on the spine, wherein the region is bounded on a first side by a posterior surface of a vertebral body of a vertebra, and wherein the region is bounded on a second side located at a distance between substantially one-third and substantially one-half through the vertebral body from the posterior surface to an anterior surface of the vertebral body.

* * * * *